United States Patent [19]

Brownscombe et al.

[11] Patent Number: 5,194,244

[45] Date of Patent: Mar. 16, 1993

[54] BASIC ALKALI METAL-ZEOLITE COMPOSITIONS

[75] Inventors: Thomas F. Brownscombe, Houston; Lynn H. Slaugh, Cypress, both of Tex.

[73] Assignee: Shell Oil Company, Houston, Tex.

[21] Appl. No.: 354,586

[22] Filed: May 22, 1989

Related U.S. Application Data

[63] Continuation-in-part of Ser. No. 275,169, Nov. 23, 1988, abandoned.

[51] Int. Cl.$^5$ ............................................. C01B 33/34
[52] U.S. Cl. .................................... 423/700; 423/716
[58] Field of Search ................ 423/329, 328, 700, 716; 502/60

[56] References Cited

U.S. PATENT DOCUMENTS

| | | | |
|---|---|---|---|
| 3,013,986 | 12/1961 | Castor | 252/455 |
| 4,140,726 | 2/1979 | Unland et al. | 260/668 B |
| 4,822,825 | 4/1989 | Bhattacharya et al. | 518/714 |

OTHER PUBLICATIONS

Hathaway et al., "Base Catalysis by Alkali-Modified Zeolites", J. Cat., 116, 263–284 (1989).
Barthomeuf et al., "Basicity and Basic Properties of Zeolites", Materials Chemistry and Physics, 18 (1988) 553–575.
Martens et al., "Sodium Clusters in Large Pore Zeolites as Basic Catalysts", 1988.
Rabo et al., "Studies of Cations in Zeolites", 1966.
Martens et al., "Preparation and Catalytic Properties of Ionic Sodium Clusters in Zeolites", Nature, 315, 568–570 (1985).
Yoon et al., "Novel Synthesis of Ionic Clusters (Na$_4^{3+}$) in Zeolites", J. Chem. Soc., Chem. Commun., 510–511 (1988).
Harrison et al., "Ionic and Metallic Clusters of the Alkali Metals in Zeolite Y", J. Solid State Chem., 54, 330–341, Feb. 1984.
Martens et al., "Sodium Clusters in Zeolites as Active Sites for Carbanion Catalyzed Reactions", 1986.
Engelhardt et al., "Alkylation of Toluene with Methanol on Commercial X Zeolite in Different Alkali Cation Forms", J. Cat., 107, 296–306, 1987.

*Primary Examiner*—Gary P. Straub
*Assistant Examiner*—Stuart L. Hendrickson

[57] ABSTRACT

This invention relates to basic compositions comprising a zeolite and an alkali metal compound wherein the sum of the amount of the alkali metal in the compound plus any metal cation exchanged into the zeolite is in excess of that required to provide a fully metal cation-exchanged zeolite. This invention further relates to methods for preparing the instant compositions. In a preferred embodiment the instant compositions are prepared by impregnating a zeolite with a solution of an alkali metal salt wherein said alkali metal impregnated in the zeolite is in excess of that required to exchange out the ion exchangable sites present in the zeolite, drying the resultant impregnated material and then calcining the resultant composition.

8 Claims, No Drawings

BASIC ALKALI METAL-ZEOLITE COMPOSITIONS

This application is a continuation-in-part of application Ser. No. 275,169, filed Nov. 23, 1988.

FIELD OF THE INVENTION

This invention relates to basic alkali metal-containing zeolite compositions and methods for their preparation.

BACKGROUND OF THE INVENTION

Zeolites are crystalline aluminosilicate minerals of a cage-network structure with pores a few angstroms in diameter. Some of the common materials, such as zeolite Y (faujasite) or zeolite A have a three dimensional structure with pore intersections ("supercages") somewhat larger than the pore size. Others such as zeolite L have channels with diffusional cross connections. Zeolites are useful as shape selective adsorbents for a variety of organic molecules and shape selective catalysts for a variety of chemical processes.

Levels of hydration of zeolites determine the number of Si—OH and Al—OH species present. The interaction of such hydroxyl groups with the aluminum oxide centers is generally thought to yield protonic (Bronsted) acid sites, while the aluminum oxide centers themselves are capable of serving as electron acceptor (Lewis acid) sites. Normal zeolitic materials have acid activity, and even if they are neutralized with base, such as with the conversion of H-zeolite to Na-zeolite, they retain some acid character. Some references consider zeolites exchanged with alkali metal cations to have some soft base sites, with an excess of acidic sites and some basic sites coexisting simultaneously. See, for example, Barthomeuf et. al., "Basicity and Basic Catalytic Properties of Zeolites", *Materials Chemistry and Physics*, 18(1988) 553–575. Further see Unland et. al., U.S. Pat. No. 4,140,726, issued Feb. 20, 1979, particularly at column 5, lines 39–44. However, neither of these references teach the use of alkali metal compounds in conjunction with a zeolite wherein the amount of alkali metal exceeds the exchange capacity of the zeolite. The acidic properties of zeolites allow them to be used to catalyze acid-catalyzed reactions such as cracking, rearrangements, alkylation of aromatic rings, etc. However, since all known zeolites, including ion exchanged materials, exhibit acid catalytic properties, it would thus be of considerable economic importance to produce materials having the narrow channels and potential for shape selective catalysis of zeolites wherein the basic properties of such materials predominated over the acidic properties, if any, present in the materials. Such materials would be useful for a variety of reactions such as side chain alkylation of aromatics, olefin oligomerization, selective oxidation, condensations and double bond isomerization without skeletal rearrangement which are difficult to achieve with normal acid zeolites.

SUMMARY OF THE INVENTION

This invention relates to basic compositions comprising a zeolite and an alkali metal compound wherein the sum of the amount of the alkali metal in the compound plus any metal cation exchanged into the zeolite is in excess of that required to provide a fully metal cation-exchanged zeolite. This invention further relates to methods for preparing the instant compositions. In a preferred embodiment the instant compositions are prepared by impregnating a zeolite with a solution of an alkali metal salt wherein said alkali metal impregnated in the zeolite is in excess of that required to exchange out the ion exchangable sites present in the zeolite, drying the resultant impregnated material and then calcining the resultant composition. Preferred alkali metal salts used in the impregnation are those which at least partially decompose in the presence of the zeolite to oxides or oxidic compounds upon heating to temperatures below about 850° C. Preferred calcining conditions generally range from about 150° C. to about 850° C. in neutral or oxidizing atmospheres.

It is an object of this invention to provide alkali metal-zeolite compositions which are basic in nature and would be particularly suitable for the adsorption of acidic gases and for the catalysis of base-catalyzed reactions. The instant compositions are also useful as supports for other catalytic components.

DETAILED DESCRIPTION OF THE INVENTION

Essentially any crystalline zeolitic aluminosilicate can be employed to prepare the compositions of the instant invention. The zeolites can include both synthetic and naturally occurring zeolites. Illustrative of the synthetic zeolites are Zeolite X, U.S. Pat. Nos. 2,882,244; Zeolite Y, 3,130,007; Zeolite A, 2,882,243; Zeolite L, Bel. 575,117; Zeolite D, Can. 611,981; Zeolite R, 3,030,181, Zeolite S, 3,054,657; Zeolite T, 2,950,952; Zeolite Z, Can. 614,995; Zeolite E, Can. 636,931; Zeolite F, 2,995,358; Zeolite O, 3,140,252; Zeolite W, 3,008,803; Zeolite Q, 2,991,151, Zeolite M, 2,995,423; Zeolite H, 3,010,789; Zeolite J, 3,001,869; Zeolite W, 3,012,853; Zeolite KG, 3,056,654; Zeolite SL, Dutch 6,710,729; Zeolite Omega, Can. 817,915; Zeolite ZK-5, 3,247,195; Zeolite Beta, 3.308,069; Zeolite ZK-4, 3,314,752; Zeolite ZSM-5, 3,702,886; synthetic mordenite; the so-called ultrastable zeolites of U.S. Pat. Nos. 3,293,192 and 3,449,070; and the references cited therein, incorporated herein by reference. Other synthetic zeolites are described in the book "Zeolite Molecular Sieves-Structure, Chemistry and Use," by Donald W. Breck, 1974, John Wiley & Sons, incorporated by reference herein. Illustrative of the naturally occurring crystalline zeolites are analcime, bikitaite, edingtonite, epistilbite, levynite, dachiardite, erionite, faujasite, analcite, paulingite, noselite, ferrierite, heulandite, scolecite, stilbite, clinoptilolite, harmotone, phillipsite, brewsterite, flakite, datolite, chabazite, gmelinite, cancrinite, leucite, lazurite, scolecite, mesolite, ptilolite, mordenite, nepheline, natrolite, scapolite, thomsonite, gismondine, garronite, gonnardite, heulandite, laumontite, levynite, offretite, yugawaralite. Descriptions of certain naturally occurring zeolites are found in the aforementioned book by Breck, in the book "Molecular Sieves-Principles of Synthesis and Identification", R. Szostak, Van Nostrand Reinhold, New York, 1989, both incorporated by reference herein, and in other known references. These zeolites may be in the hydrogen form or may be partially or fully exchanged with ammonium or metal ions.

As used herein, the term "compound" as applied to alkali metal refers to the combination of alkali metal with one or more elements by chemical and/or physical and/or surface bonding, such as ionic and/or covalent and/or coordinate and/or van der Waals bonding, but specifically excludes that bonding involved between an alkali metal and a zeolite when such alkali metal is located in a cation exchange site of the zeolite. The term "ionic" or "ion" refers to an electrically charged moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions. The term "oxidic" refers to a charged or neutral species wherein an element such as an alkali metal is bound to oxygen and possibly one or more different elements by surface and/or chemical bonding. This, an oxidic compound is an oxygen-containing compound, which also may be a mixed, double, or complex surface oxide. Illustrative oxidic compounds include, by way of non-limiting example, oxides (containing only oxygen as the second element), hydroxides, nitrates, sulfates, carboxylates, carbonates, bicarbonates, oxyhalides, etc, as well as surface species wherein the alkali metal is bound directly or indirectly to an oxygen either in the substrate or the surface. "Surface" as applied to zeolites and the instant compositions refers to external surface as well as the internal pore surface, the internal surface being both the surface of the macro pores resulting from the agglomeration of individual particles or crystallites as well as the surface of the mesopores and micropores and supercages that result from the intrinsic zeolite crystal structure. The term "salt" as used in the instant specification and claims is meant to encompass a single salt as well as mixtures of two or more salts. The term "alkali metal" is used herein as a descriptor of the elements of Group IA of the Periodic Table of the Elements (Li, Na, K, Rb, Cs, Fr). Alkali metal herein does not refer the element in the metallic or zero valent state, but rather is a shorthand use for the element in the positive valent state, that is, it will be understood to be combined as a salt, compound, complex, etc. The term "basic" refers to having the characteristic of a base; e.g., when placed in a solution, a basic material will have a pH consistent with a base rather than an acid and, if a catalyst, will catalyze chemical reactions that are catalyzed by bases.

The alkali metal salts that are suitable for preparing the compositions of the instant invention are any salts that can be dissolved in a suitable impregnating solution or which can be melted to form their own impregnating solution or which can be sublimed and condensed on the zeolite. Illustrative but non-limiting examples of suitable salts are alkali metal bicarbonates, carbonates, chlorates, perchlorates, hypochlorites, cyanates, hydroxides, iodates, nitrates, nitrites, sulfates, hydrogen sulfates, sulfites, thiocarbonates, thiocyanates, thiosulfates, alkoxides, carboxylates, sulfonates and the like. Salts which can be solubilized in a suitable solution are preferred. Preferred salts are those which have an oxygen-containing anion or oxyanion. Useful salts are those which decompose at least in part upon calcination in the presence of the zeolite to provide an alkali metal-oxygen-containing moiety (Na—O—), that is, produce an oxidic compound. When the alkali metal salt is associated with an anion which does not contain oxygen it is necessary that the subsequent calcination be carried out in an oxygen-containing atmosphere and that the salt decompose to provide the alkali metal-oxygen-containing moiety, that is, produce an alkali metal oxidic compound. Decomposition can be indicated by the evolution of gases such as carbon oxides, nitrogen oxides, sulfur oxides etc. Decomposition will also be indicated by disappearance at least in part of the particular anionic form associated with the alkali metal in the impregnation liquid. For example, when carboxylates and alkoxides are calcined the carboxylate and alkoxide moiety associated with the alkali metal will decompose giving off carbon oxides and/or water and/or hydrocarbons, thereby disappearing at least in part. Particularly preferred salts to be used in an impregnating solution are bicarbonates, carbonates, acetates and oxalates, particularly of potassium. Mixtures of alkali metal salts, that is, two or more salts with differing anions, differing cations or differing anions and cations can be utilized to prepare the impregnated zeolite.

Strongly basic salts such as the hydroxides have a tendency to degrade the crystal structure of zeolites. Thus, it is preferred that compounds used to prepare the instant compositions exclude the alkali metal hydroxides.

One method that can be used to prepare the compositions of the instant invention involves the use of molten alkali metal salt to impregnate the zeolite. In this method a suitable salt, that is, one melting below about 850° C.; is melted and the zeolite is added to the molten salt or the molten salt is added to the zeolite causing the molten salt to impregnate the pores of the zeolite. A very suitable impregnation technique is to utilize that amount of molten salt that is equal to or less than that amount of molten salt that will just fill the pores of the zeolite. Alternatively, zeolite particles can be immersed in a molten salt bath to cause impregnation of the molten salt into the zeolite followed by separation of the excess molten salt from the zeolite, say by filtration, centrifugation or washing. Alternatively, zeolite particles can be coated with finely divided particles of a suitable alkali metal salt and heated to above the melting point of the salt, causing the molten salt to impregnate the pores of the zeolite. After impregnation, the impregnated zeolite is calcined to produce the composition of the instant invention. The calcining temperature may be the same or lower than the impregnating temperature but frequently it is higher. Drying is not required when the molten salt technique is utilized, but may be utilized to remove residual water remaining in the zeolite. The impregnation and calcination can be carried out in one continuous step or sequence.

Another method is to use a sublimable alkali metal salt. In this method a suitable salt is sublimed at above its sublimation temperature to produce a vaporous salt and the resulting vapor is contacted with the zeolite maintained at a temperature below the sublimation temperature of the salt thereby causing the vapor to condense upon and within the pores of the zeolite thereby impregnating it. Calcination follows to prepare the compositions of the instant invention. Drying before calcination is not required in this case, but may be utilized to remove residual water in the zeolite. The impregnation and calcination can be carried out in one continuous step or sequence.

Most conveniently and preferably, solutions of alkali metal salts are used to impregnate the zeolites. The solvents utilized to dissolve the salts may be organic or inorganic. The only requirement is that the desired salt be soluble in the particular solvent. Hydroxylic solvents are preferred. Water is a particularly preferred solvent. The lower alkanols are also particularly suitable for use with salts having strong basicity in water in order to minimize base-zeolite structure interactions during the impregnation process. Organic solvents are particularly useful as solvents for alkali metal salts which have organic ionic components such as carboxylate, sulfonate, alkoxide, etc. Organic solvents are also useful for inorganic alkali metal salts. Alkali metal salts having a low solubility in an organic solvent can be used with that solvent to provide small, but well controlled amounts of alkali metal to the zeolite while minimizing solvent-base-zeolite structure interactions. Illustrative, but nonlimiting examples of organic solvents include alcohols, including polyhydric alcohols, ethers, esters, ketones, amides, sulfoxides and chloro/fluorohydrocarbons such as the various freons. Specific illustrative examples include methanol, ethanol, glycol, dimethyl ether, methyl acetate, methylethyl ketone, dimethyl formamide ("DMF"), dimethyl sulfoxide ("DMSO"), N-methyl pyrrolidone ("NMP"), hexamethylphosphoramide ("HMPA"), dichlorodifluoromethane, methyl chloride, ethylene dichloride, ethylene carbonate, etc. Illustrative, but not-limiting examples of inorganic solvents include water, liquid ammonia, liquid carbon dioxide, liquid sulfur dioxide, carbon disulfide, carbon tetrachloride, etc. Mixtures of solvents which are mutually miscible may be utilized.

Single or multiple impregnations may be used. When multiple impregnations are used intermediate drying steps, optionally followed by calcination may be utilized. Generally any amount of impregnating liquid can be used in the impregnation process. For example, the zeolite can be dipped into a large excess (compared to the pore volume of the zeolite), removed and shaken of excess liquid. Alternatively, an amount of impregnating liquid considerably less than the pore volume can be sprayed onto an agitated bed of zeolite. For purposes of economy, control and other reasons, the volume of impregnating liquid will preferably range from about the pore volume to about four or five times, preferably about twice the pore volume of the zeolite to be impregnated. Preferably a "dry" impregnation technique is utilized wherein just that amount of impregnating solution is used which will just fill the pores of the zeolite.

The concentration of alkali metal salts in the impregnating solution is not critical and is selected, inter alia, on the basis of the zeolite used, the amount of ion exchange capacity present in the zeolite, the degree of basicity of the final product desired, the impregnation solvent used and the type of impregnation utilized, that is, multiple of single. Concentrations of alkali metal salt(s) in the impregnating solution will typically range from about 0.01 moles per liter to the solubility limit of the salt(s). A suitable range is from about 0.01 to about 20 moles per liter, more preferably from about 0.1 to about 10 moles per liter.

The amount of alkali metal which is impregnated into the zeolite must be in excess of that which would provide a fully cation-ion exchanged zeolite. For example, if the starting zeolite were completely in the hydrogen form and had an ion exchange capacity of 12% (basis Na$_2$O), then the amount of alkali metal impregnated (basis Na$_2$O) must exceed the 12%. If the starting zeolite were one which had already been 80% exchanged with a metal cation, the amount of alkali metal to be added by impregnation would be in excess of that amount required to exchange the remaining 20%. If the starting zeolite were fully metal cation exchanged, then any amount of alkali metal in the impregnating solution would suffice. It is to be understood that impregnation of a partially or fully cation-exchanged zeolite will most likely result in some counter ion exchange between the impregnating alkali metal cation(s) and the cations already present in the zeolite, but the resulting composition will still be within the scope of the instant invention in having an excess of alkali metal present over the amount exchanged into the fully exchanged zeolite. When the amount of impregnating solution that is utilized is such that after impregnation no excess solution is removed, then the amount of alkali metal salt in the impregnating solution will be the same as the amount impregnated into the zeolite. When an amount of impregnating solution is used that requires that an excess amount of solution must be removed, for example, by filtration or centrifugation, from the impregnated zeolite after impregnation, then the amount of alkali metal in the impregnating solution will exceed the amount of alkali metal impregnated into the zeolite. In this latter case, the amount of alkali metal impregnated into the zeolite can be determined by a knowledge of concentration of alkali metal in the impregnating solution before the impregnation, the concentration of alkali metal in the excess solution removed from the impregnated zeolite and the amount of solution remaining after impregnation (the excess). Alternatively, the impregnated zeolite can be analyzed for alkali metal content.

The compositions of the instant invention which comprise a zeolite and an alkali metal compound can be divided into four somewhat arbitrary classes, depending on the amount of alkali metal compound that is present in the composition. In order of increasing basicity, there are low base, low-intermediate base, high-intermediate base and high base compositions. The higher the basicity of the instant compositions, the higher will be the suppression of any acid function of the zeolite. The calculations of the ranges and limits for these various classes are to be made considering the alkali metal as the metal (ion) and any metal(s) exchanged into the zeolite as the (ionic) equivalent of an alkali metal.

In general it is preferred to have a slight excess of alkali metal present. When considering as a basis for calculation the zeolite having no cations exchanged therein, the preferred compositions will have the sum of the alkali metal in the alkali metal compound and any metal cation exchanged into the zeolite being greater than 1, preferably greater than about 1.05, more preferably greater than about 1.1, even more preferably greater than about 1.15, even more preferably greater than about 1.2, even more preferably greater than about 1.5 and even more preferably greater than about 2 times the amount required to provide a fully cation-exchanged zeolite (or times the exchange capacity). When considering the fully cation-exchanged zeolite as a basis for calculation, the amount of alkali metal in the alkali metal compound is greater than zero, preferably greater than about 0.05, more preferably greater than about 0.1, even more preferably greater than about 0.15, even more preferably greater than about 0.2, even more preferably greater than about 0.5 and even more preferably greater than about 1 times the amount of alkali metal that would be required to provide a fully metal cation-exchanged zeolite (or times the exchange capacity).

When considering as a basis for calculation the zeolite having no cations exchanged therein, the low base compositions will have the sum of the alkali metal in the alkali metal compound and any metal cation exchanged into the zeolite ranging from greater than to about 1.2 times the amount required to provide a fully cation-exchanged zeolite (or times the exchange capacity). When considering the fully cation-exchanged zeolite as a basis for calculation, the amount of alkali metal in the alkali metal compound is greater than to about 0.2 times the amount of alkali metal that would be required to provide a fully metal cation-exchanged zeolite (or times the exchange capacity).

When considering as a basis for calculation the zeolite having no cations exchanged therein, the low-intermediate base compositions will have the sum of the alkali metal in the alkali metal compound and any metal cation exchanged into the zeolite ranging from about 1.2 to about 1.5 times the amount required to provide a fully cation-exchanged zeolite (or times the exchange capacity). When considering the fully cation-exchanged zeolite as a basis for calculation, the amount of alkali metal in the alkali metal compound ranges from about 0.2 to about 0.5 times the amount of alkali metal that would be required to provide a fully metal cation-exchanged zeolite (or times the exchange capacity).

When considering as a basis for calculation the zeolite having no cations exchanged therein, the high-intermediate base compositions will have the sum of the alkali metal in the alkali metal compound and any metal cation exchanged into the zeolite ranging from about 1.5 to about 2 times the amount required to provide a fully cation-exchanged zeolite (or times the exchange capacity). When considering the fully cation-exchanged zeolite as a basis for calculation, the amount of alkali metal in the alkali metal compound ranges from 0.5 to about 1 times the amount of alkali metal that would be required to provide a fully metal cation-exchanged zeolite (or times the exchange capacity).

When considering as a basis for calculation the zeolite having no cations exchanged therein, the high base compositions will have the sum of the alkali metal in the alkali metal compound and any metal cation exchanged into the zeolite ranging from about 2 times the amount required to provide a fully cation-exchanged zeolite (or times the exchange capacity) to the limit of alkali metal compound that can be physically impregnated into the zeolite, which in a preferred embodiment is about 3.5 times the amount required to provide a fully cation-exchanged zeolite (or times the exchange capacity). When considering the fully cation-exchanged zeolite as a basis for calculation, the amount of alkali metal in the alkali metal compound ranges from about 1 times the amount of alkali metal that would be required to provide a fully metal cation-exchanged zeolite (or times the exchange capacity) to the limit of alkali metal compound that can be physically impregnated into the zeolite, which in a preferred embodiment is about 2.5 times the amount required to provide a fully cation-exchanged zeolite (or times the exchange capacity).

When considered in terms of those cases where increasing basicity is desired, and when considered in terms of the non-cation exchanged zeolite as a basis for calculation, the sum of alkali in the alkali metal compound and any metal cation exchanged into the zeolite is greater than 1, preferably greater than about 1.2, more preferably greater than about 1.5 and even more preferably greater than about 2 times the amount required to provide a fully cation-exchanged zeolite (or times the exchange capacity). When considering the fully cation-exchanged zeolite, the amount of alkali metal in the alkali metal compound is greater than zero, preferably greater than about 0.2, more preferably greater than about 0.5, and even more preferably greater than 1 times the amount of alkali metal that would be required to provide a fully metal cation-exchanged zeolite.

After impregnation utilizing an impregnating solution, the impregnated zeolite is dried to remove the solvent of the impregnating solution. The drying conditions are not critical to the instant invention. Drying may be carried out at atmospheric pressure, superatmospheric pressure or under vacuum. It also may be carried out by passing a dry (with regard to the impregnating solvent) gas over a bed of the zeolite. Drying temperatures will depend upon the solvent used. For those solvents that are liquid at low temperatures, such as liquid carbon dioxide or liquid sulfur dioxide, the drying temperature can be relatively low, that is, below room temperature. For the more conventional solvents which are liquid at or above room temperature, higher temperatures will be used. For these solvents temperatures will typically range from about room temperature to about 200° C. In most cases drying temperatures will be less than about 200° C., preferably less than 150° C. Drying times are dependent upon the drying temperature and pressure, typically from about one minute to about twenty hours, although longer or shorter times can be utilized. Drying atmospheres and pressures are normally not critical. The drying atmosphere may be neutral, oxidizing, reducing or a vacuum.

After drying to remove an impregnating solvent or after impregnation by means of a molten or vaporous salt, the impregnated zeolite is calcined at elevated temperatures to provide the composition of the instant invention. Calcination conditions will range from about 150° C. to about 850° C.; preferably from about 200° C. to about 750° C.; and more preferably from about 200° C. to about 600° C. Calcining times are dependent on the calcining conditions selected and typically range from about one minute to about twenty hours, although longer or shorter times can be utilized. Calcining conditions and times are also adjusted according to the thermal stability. Calcination conditions should not be so extreme as to cause extreme loss of zeolite crystallinity. Calcining atmospheres may be neutral, oxidizing or reducing. When the impregnating salt has an anionic component which does not contain oxygen, an oxygen-containing calcining atmosphere is utilized. When the calcined composition is a catalyst or a catalyst support, particular calcining atmospheres may be called for. For example, when certain catalytic metals need to be present in the reduced state, a reducing atmosphere is utilized. Barring special circumstances, neutral atmospheres such as provided by nitrogen and oxidizing atmospheres such as provided by air are preferred.

In a preferred embodiment when using an impregnation solution, the drying and calcining steps are combined into one integrated process step. In this combined step the impregnated zeolite is heated through the lower temperatures at a rate slow enough that physical disruption of the zeolite does not occur due to rapid volatilization of the solvent from the impregnation. After the solvent has been removed, the zeolite is then heated to the desired calcining temperature, maintained for the desired calcining time and then cooled to room temperature.

The calcining is one of the critical steps in the instant invention that leads to the instant basic compositions. The exact form of the alkali metal after calcination in the instant compositions is not known. Without intending to limit the scope of the instant invention, it is believed that the alkali metal(s) is present as one or more alkali metal oxidic compounds. It is speculated that the alkali metal compound(s) are probably in the form of a surface oxide or multiple surface oxides with the zeolite, in particular with the aluminum and/or silicon and/or oxygen of the zeolite lattice, possible in combination with species contained in or formed from the impregnation solution or during the calcination process.

The calcination produces a composition which is basic and this basic nature is thought to derive from the particular nature of the alkali metal compound present after calcination. This basic nature can be seen from the fact that instant compositions when placed in a solvent produce effects that are basic rather than acidic in nature. This can been seen by the use of suitable chemical or electrochemical indicators. The basic nature of the instant compositions can also be seen from the fact that they will catalyze or carry out chemical reactions that are catalyzed or carried out by bases. For example, the dehydrochlorination of chlorohydrocarbons such as 1-chlorooctane, are well known to be carried out by bases and the instant compositions also carry out this reaction.

The basicity of the instant compositions can be determined in various ways. For example, it can be determined by measuring the extent to which various base-catalyzed reactions are carried out in the presence of of the instant compositions. Another method is to place the instant composition in a solvent and measure the resulting pH by use of chemical or electrochemical indicators. A specific example would involve placing 20 mg of composition in 2 g of water and using a pH meter or pH paper to measure the resulting pH. Another method is to use various indicators in non-aqueous solutions and compare the indicator response caused by the instant compositions with the indicator response caused by selected reference samples. Two such suitable indicators are 4-nitroaniline dissolved in dimethyl sulfoxide ("DMSO", 0.1 g/cc) or in benzene (0.1 g/cc) and 4-chloroaniline dissolved in benzene (0.1 g/cc) or in DMSO (0.1 g/cc). Examples of indicator responses with various reference samples is shown in Table 1 below.

TABLE 1

| Reference | 4-nitroaniline/DMSO | 4-chloroaniline/benzene |
|---|---|---|
| $NaNH_2$ | very dark blue | purplish brown |
| KOH | dark blue | creme |
| NaY-Zeolite | yellow | creme |
| amorphorous $SiO_2$ | faint yellow | creme |

In general terms the compositions of the instant invention comprise a basic, structured, that is a zeolitically structured, alkali metal-containing aluminosilicate containing in compound form an excess of alkali metal over that necessary to provide a fully metal cation-exchanged aluminosilicate. More specifically, the instant compositions comprise a zeolite and an alkali metal compound, particularly an oxidic compound, wherein the sum of the amount of the alkali metal in the compound plus any metal cation exchanged into the zeolite is in excess of that required to provide a fully metal cation-exchanged zeolite. The instant compositions will contain at least a portion of their pore volume in micropores in the range of from about four to about twelve angstroms. The instant compositions react as bases when placed in solvents and catalyze base-catalyzed reactions. In a preferred embodiment for shape selective catalysis, the alkali metal compound is substantially located on the internal pore surfaces of the zeolite rather than the external surfaces.

The instant compositions retain at least a portion of a crystalline zeolite structure. The term "crystalline" is employed herein to designate an ordered structure capable of being detected by electrooptical or diffraction techniques, normally by X-ray diffraction, giving a consistent crystallographic pattern. Such an ordered structure can persist even after some of the structural silica or alumina is removed from the crystal lattice, as by leaching with acids, or with bases such as might occur during the impregnation process, or by other physical or chemical methods. Sometimes the ordered structure may become so attenuated by these or other means as to fail to diffract X-rays, but in such cases other electrooptical methods, such as electron beam diffraction may be utilized. In other cases the crystallite size may become so small that diffraction effect may become so diffuse that the amount of crystalline structure may be difficult to detect or determine. In this latter instance, however, the retention of a large surface area after chemical and/or physical processing will indicate the retention of a certain amount crystalline zeolite structure. Thus these latter materials are still structured aluminosilicates as opposed to amorphous aluminosilicates and are within the scope of the instant invention.

The compositions of the instant invention find many uses. They are useful as adsorbents. They ca be used, for example, to adsorb acidic gases or vapors from a vapor phase, or to adsorb acidic species from a liquid phase.

The instant compositions can also serve as catalysts or catalyst supports for other catalytic components. Catalytic components may be incorporated into the instant compositions at any stage of their preparation, that is, prior to, during and after the conversion of the starting zeolite to final basic composition. Large numbers of materials can be added to the compositions of the instant invention in order to make catalysts. Illustrative but non-limiting examples include the transition metals (atomic nos. 21-29, 39-47, 72-79); Group IIB metals (atomic nos. 30, 48, 80); Group IIIA metals (atomic nos. 5, 13, 31, 49, 81); Group IVA metals (atomic nos. 14, 32, 50, 82); Group VA metals (atomic nos. 15, 33, 51, 83); Group VIA metals (atomic nos. 34, 52); the lanthanide metals (atomic nos. 57-71), as well as their oxides, sulfides, halides, salts, complexes, compounds and the like.

Illustrative but non-limiting examples of organic chemical reactions for which the instant compositions will find use as catalysts include double bond isomerization, dehydrogenation, cyclization of polyenes, H-D exchange, condensation, side chain alkylation of alkyl benzenes, olefin dimerization, olefin oligomerization, dehydrohalogenation, cleavage coupled with oxidation, oxidation, reduction/elimination, nucleophilic addition, etc.

Illustrative but non-limiting examples of organic chemical reactions for which the instant compositions when combined with other catalytic components will find use are illustrated in Table 2 below.

TABLE 2

| Catalytic Component | Reaction |
|---|---|
| Sc | C—H activation |
| V | oxidation |
| Cr | oxidation, coupling, cyclization, reductive |

TABLE 2-continued

| Catalytic Component | Reaction |
|---|---|
| | cleavage |
| Mn | oxidation |
| Fe | oxidation, olefin isomerization, cyclization, reduction, halogenation |
| Co | oxidation, hydroformylation, hydrogenation, olefin isomerization, dimerization |
| Ni | hydrogenation, oligomerization, isomerization, carbonylation, dimerization, coupling, cyclization |
| Cu | oxidation, hydrogenation, coupling, cyclization, decarboxylation, cyanoethylation, halogenation |
| Y | oxidation, C—H activation |
| Nb | oxidation, olefin isomerization |
| Mo | oxidation, olefin isomerization |
| Ru,Rh,Pd | CO activation, oxidation, amination, hydrogenation, olefin isomerization, isomerization, cyclization |
| Ag | oxidation, hydrogenation, rearrangement, hydroxylation |
| La—Lu | oxidation, condensation, amination, dehydrogenation, oligomerization |
| Re | oxidation, hydration |
| Os | oxidation, epoxidation, hydrogenation |
| Pt | C—H activation, hydrogenation, CO activation, isomerization |
| Bi | oxidation, suppression of dehydrogenation |
| Th,U | CO activation, oxidation |
| W | oxidation, activation |
| Sb | combustion suppression |
| Sn | weak acid binding site, reduction |
| Ir | hydrogenation, olefin isomerization |
| Hg | hydrogenation, oxidation, hydration, halogenation |
| Pb | oxidation, coupling, cyclization, decarboxylation, cleavage |
| Ti | oxidation, dimerization, rearrangements, isomerization |
| Tl | oxidation |
| Zn | ether cleavage |
| Zr | alkylation |

When catalytic components are added to the instant compositions numerous factors will be considered by one skilled in the art when preparing the combination of catalytic components and instant compositions. Non-limiting examples of these factors include pore structure; ease of activation; number of base sites; location and type of catalytic components; stability of the catalyst(temporal, thermal, hydrolytic, etc.); polarity (ionization ability) of zeolitic pore/cage; binding affinity (lipophilicity or hydrophilicity) of zeolitic pore/cage; use of promoters or activators to modify catalytic effects; shape selectivity, presence or absence of dual channel network; etc.

The compositions of the instant invention, alone or in combination with other catalytic components, may be distributed throughout an inert inorganic diluent which also may serve as a binder. Non-limiting examples of such diluents include aluminas, silicas, silica-aluminas, charcoal, pumice, magnesia, zirconia, keiselguhr, fullers' earth, silicon carbide, clays and other ceramics. In a preferred use of binders the instant zeolitic compositions are intimately mixed a finely divided, hydrous, refractory oxide of a difficulty reducible metal. The term "hydrous" is used to designate oxides having structural surface hydroxyl groups detectable by infrared analysis. The preferred oxides are alumina, silica, magnesia, beryllia, zirconia, titania, thoria, chromia, and combinations thereof such silica-alumina, silica-magnesia, and the like. Naturally occurring clays comprising silica and alumina may also be utilized, preferably after acid treatment. The metal oxide can be combined with the instant compositions as a hydrous sol or gel, an an anhydrous activated gel, a spray dried powder or a calcined powder. In one modification a sol or solution of the metal oxide precursor such as an alkali metal silicate or aluminate can be precipitated to form a gel in the presence of the compositions of the instant invention. When less hydrous form of the metal oxide are combined with the instant compositions, essentially any method of effecting intimate admixture of the components may by utilized. One such method is mechanical admixture, e.g., mulling, which involves admixing the instant compositions in the form of a powder with the slightly hydrous, finely divided form of the metal oxide. The diluent or binder may be added to the instant compositions at any point in their preparation, that is, before, during or after impregnation, drying and/or calcination.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The following illustrative embodiments are provided for illustration and are not to be construed as limiting the invention.

ILLUSTRATIVE EMBODIMENTS

The following illustrative embodiments, which are also summarized in Table 3, are grouped according to typical example types, described below. Table 3 also provides selected reference materials and comparative examples along with certain physical properties and basicity test results. Table 3 also provides data relative to compositions prepared similar to examples A through M along with the variations used in starting zeolites, impregnating solutions, impregnating salts, impregnating conditions, resulting selected properties and basicity test results. It is apparent that many variations and extensions of these examples may be performed by one skilled in the art to achieve results within the scope of the instant invention. These examples are provided only to illustrate the invention, not to limit it.

EXAMPLE A

Low Level Impregnation of Salt Into Zeolite 50 g Baylith CP-190 NaY zeolite was impregnated with 2.12 g KOH (Aldrich) dissolved in 20 cc water. The zeolite was mixed in a dish during impregnation, then dried 1 hour at 100° C. in a vacuum oven. This material is B21 in Table 3.

36 g of the KOH/NaY (B21) was placed in a vycor tube in an upright furnace. With a slow nitrogen flow through the tube, the furnace was heated to 550° C. over a period of 30 minutes. After 1 hour, the furnace was turned off and allowed to cool, while still under flowing nitrogen. The catalyst was removed and labelled B22 in Table 3.

EXAMPLE B

Calcination of Previously Impregnated Zeolite 84.07 g Baylith CP-190 NaY zeolite was dried for 2 hours in a 190° C. vacuum oven with a low nitrogen bleed. 50 g of this dried Nay was impregnated with 1.9 g potassium carbonate (MCB ACS reagent) dissolved in 25 cc water. The zeolite was mixed in a dish during impregnation, then dried at 100° C. in a vacuum oven with a low nitrogen bleed. The dried impregnated zeolite was then stored in a dry box, labelled A1 in Table 3.

Three months later, 8.59 g of the masterbatch material A1 was placed in a fritted tube in the dry box. This tube was brought out and placed in an upright heating mantle. The nitrogen flow was set at 90 cc/min and the mantle was heated to 450° C. over a period of 40 minutes. After 116 minutes, the mantle was turned off and allowed to cool while still under flowing nitrogen. The cooled tube was sent into the dry box, where the zeolite was unloaded and stored as material B3 in Table 3.

EXAMPLE C

Impregnation With a High Loading, With Solvent Greater In Amount Than Salt In the Impregnating Solution 20.02 g 4A zeolite was impregnated with 4.53 g sodium carbonate dissolved in 10 cc water. The zeolite was mixed in a dish during impregnation, then dried 16 hours at 70° C. in a vacuum oven. The result is material B6 of Table 3.

10 g of material B6 was placed in a fritted tube in an upright heating mantle. The nitrogen flow was set at 90 cc/min and the mantle was heated to 450° C. over a period of 50 minutes. After 115 minutes, the mantle was cooled while still under flowing nitrogen. The resulting material is B7 in Table 3.

EXAMPLE D

Zeolite Slurried In Salt Solution and Dried With the Solution Left In It 100 cc potassium acetate solution (29.74 g Aldrich acetic acid, potassium salt dissolved in 300 cc water) was added to an Erlenmeyer flask containing 10.01 g Baylith CP-190 NaY zeolite. This mixture stirred at room temperature. After 1 hour, the mixture was filtered in a fritted vacuum funnel. The resulting paste was returned to the Erlenmeyer flask with a fresh 100 cc of the potassium acetate solution. The solution was allowed to sit over the weekend, before being filtered again. Once again the paste was returned to the Erlenmeyer flask with a fresh 100 cc of the potassium acetate solution. After stirring for approximately 24 hours, it was filtered a final time. The paste was dried for 20 hours at 100° C. in a vacuum oven. The dried zeolite was pressed in bags in the isostatic press at 20,000 psi for 2 minutes. It was then ground and sieved to 16-30 mesh. The result was material C4 in Table 3.

The dried zeolite C4 was placed in a vycor tube in an upright furnace. The nitrogen flow was set at 20 cc/min, then the furnace was heated to 200° C. over a period of 15 minutes. After 35 minutes at 200° C.; the furnace was heated to 550° C. over a period of 15 minutes. After 40 minutes, the heater was turned off and allowed to cool while still under flowing nitrogen. The vycor tube was sent into the dry box and stored for about 16 hours, at which time the tube was returned to the upright furnace. The nitrogen flow was set at 30 liters/hour, then the furnace was heated to 200° C. over a period of 20 minutes. After 25 minutes the temperature was raised to 550° C.; this took a period of 11 minutes. After 2 hours, the furnace was turned off and allowed to cool while still under flowing nitrogen. The resulting material was C5 in Table 3.

EXAMPLE E

Exchange of Zeolite Followed By Impregnation 100 cc 1M cesium acetate solution (76.4 g Aldrich cesium acetate dissolved in 400 cc Barnstead deionized water) was added to a flask containing 20.02 g LZY-82 pellets (Union Carbide). After stirring for 16 hours, the liquid was decanted off the pellets. A fresh 100 cc aliquot of the 1M cesium acetate solution was added to the flask. After 2 hours, the liquid was decanted off. The addition, stirring 2 hours and decanting of liquid was repeated two more times. After the final decanting of the liquid, the pellets were vacuum filtered, then dried 85 minutes at 100° C. in a vacuum oven. This is material C20 in Table 3.

20 g of this dried material was impregnated with 1.82 g cesium acetate (Aldrich) dissolved in 1.8 cc water (Barnstead deionized). The zeolite was mixed in a dish during impregnation and allowed to sit 25 minutes, then dried 16 hours at 100° C. in a vacuum oven, becoming material C21.

The dried zeolite C21 was placed in a vycor tube in an upright furnace. The nitrogen flow was set at 15 liters/hour and the furnace heated to 200° C. After holding at 200° C. for 25 minutes, the temperature was increased to 550° C. After 2 hours, the furnace was turned off and allowed to cool while still under flowing nitrogen. The resulting material was C22 in Table 3.

EXAMPLE F

Impregnation With Amount of Salt Greater Than Amount of Solvent In Solution 35.0 g LZY-52 pellets were dried for 2 hours at 160C in a vacuum oven. 2.08 g of this dried LZY-52 was impregnated with 1.04 g of potassium acetate solution (20.38 g Aldrich potassium acetate dissolved in 10 cc Barnstead deionized water). The LZY-52 was mixed in a vial during impregnation, then dried 16 hours at 160° C. in a vacuum oven. The dried material was placed in a vycor tube in an upright furnace. The nitrogen flow was set at 400 cc/min and the furnace was heated to 200° C. over a period of 20 minutes. After 25 minutes at 200° C.; the temperature was raised (over a period of 12 minutes) to 550° C. After 2 hours, the furnace was turned off and allowed to cool while still under flowing nitrogen. 16 hours later, the nitrogen was turned off and an air (dried over Drierite) flow was stated. The air flow was set at 450 cc/min and the furnace was heated to 200° C. After 21 minutes at 200° C.; the temperature was raised to 550° C. After 2 hours, the temperature was 600° C. After 50 more minutes, the flow rate of air was reduced to 200 cc/min. After an additional 1.5 hours at 600° C.; the air flow was blocked , nitrogen flow of 100 cc/min was begun, and the heater turned off and allowed to cool. The resulting material was C24 in Table 3.

EXAMPLE G

Impregnation With Pure Water On Zeolite Previously Impregnated With Salt To Distribute the Salt Natural erionite was dried 1 hour at 150° C. in a vacuum oven. 1.05 g of this dried erionite was impregnated with 2.02 g potassium oxalate solution (16.12 g potassium oxalate dissolved in 50 cc Barnstead deionized water). The erionite was mixed in a vial during impregnation, then dried 105 minutes at 150° C. in a vacuum oven. Upon L removing from the vacuum oven, 0.60 cc Barnstead water (0.5 cc water/ g of catalyst) was added. The mixture was allowed to sit 20 minutes, then dried 1 hour at 150° C. in a vacuum oven. 0.6 cc Barnstead water was added to the material which then sat 20 minutes, and was dried 1 hour at 150° C. in a vacuum oven.

The dried material was placed in a vycor tube in an upright furnace. The nitrogen flow was set at 350 cc/min, and the furnace was heated to 200° C. After 25 minutes, the furnace temperature was raised to 550° C. After 2 hours at 500° C.; the furnace was turned off and allowed to cool, while still under flowing nitrogen. This material is listed under D7 in Table 3.

EXAMPLE H

Slurrying the Zeolite Followed By Washing

Method of preparation of the materials tested under E9 in Table 3

40 cc 2M potassium carbonate solution (138.22 g MCB potassium carbonate dissolved in 500 cc Barnstead deionized water) was added to a flask containing 4.01 g ammonium mordenite (dried 2 hours at 150° C. in a vacuum oven). After stirring 1 hour, this suspension was filtered and the solid washed with two 50 cc aliquots of Barnstead deionized water. The paste was dried 1 hour at 150° C. in a vacuum oven. The dried zeolite was returned to the flask with 40 cc 2M potassium carbonate solution. After stirring for 1 hour, it was filtered and then washed with two 50 cc aliquots of Barnstead deionized water. The paste was dried 1 hour at 150° C. in a vacuum oven.

EXAMPLE I

Molten Salt Impregnation 209 g Baylith CP-190 NaY (out of the can) was stirred with 2 liters of Barnstead deionized water. After 2 hours, it was filtered. An additional 400 cc Barnstead water was poured through the funnel. The zeolite was then dried 16 hours at 150° C. in a vacuum oven.

0.87 g cesium acetate was heated to 200° C. in a 250 ml 3-neck round bottom flask equipped with a condenser, a thermometer, a stir bar, and a heating mantle. At 200° C. all the cesium acetate appeared to be a fluid, at this point, 8.63 g of the washed NaY zeolite was added to the flask. The solid was stirred in the flask, and the temperature raised to 220° C. After 70 minutes, the heat was turned off and the flask allowed to cool. The product was FI in Table 3. After calcination in flowing nitrogen at 550° C. the material F2 was obtained.

EXAMPLE J

Impregnation With Solvent To Redistribute Salt On Previously Calcined Material 30.01 g LZY-82 (Lot #9661796179 Union Carbide powder) zeolite was impregnated with 25.09 g lithium acetate solution (20.75 g lithium acetate dihydrate dissolved in 22 cc Barnstead deionized water). The zeolite was mixed in a dish during impregnation, allowed to sit 10 minutes, then dried 30 minutes at 150° C. in a vacuum oven. The zeolite was then impregnated with an additional 13.39 g lithium acetate solution. The impregnation was done in a dish, then the zeolite dried 33 minutes at 150° C. in a vacuum oven. This was material F11. 10 cc Barnstead deionized water was added to the dried zeolite. After sitting 15 minutes, the zeolite was dried 30 minutes at 150° C. in a vacuum oven. 35.85 g of the impregnated zeolite was recovered as F12.

17.93 g of F12 was placed in a vycor tube in an upright furnace. Nitrogen flow was set at 250 cc/min, then the furnace heated to 200° C. After 25 minutes, the temperature was raised to 550° C. After 2 hours at 550° C.; the furnace was turned off and allowed to cool while still under flowing nitrogen. The product material was F13.

5 cc Barnstead water was added to 17.92 g of F12 in a dish. After sitting 25 minutes, it was dried 65 minutes at 150° C. in a vacuum oven. An additional 5 cc water was added to the zeolite. After sitting 25 minutes, it was dried 1 hour at 150° C. in a vacuum oven. An additional 5 cc water was added to the zeolite. After sitting 1 hour, it was dried 66 hours at 150° C. in a vacuum oven. The result was material F14.

5 cc Barnstead deionized water was added to 14 g of F13. This was dried 1 hour at 150° C. in a vacuum oven, yielding F15. The dried material was placed in a vycor tube in an upright furnace. The nitrogen flow rate was set at 200 cc/min and the furnace was heated to 200° C. After 23 minutes, the furnace temperature was increased to 550° C. After 2 hours at 550° C.; the furnace was turned off and allowed to cool, while still under flowing nitrogen. The product was F16 in Table 3.

EXAMPLE K

Impregnation With a Catalytic Metal Salt Followed By Impregnation With Base Progenitor 31.15 g Baylith CP-190 NaY zeolite was impregnated with 5 g ruthenium nitrosyl nitrate (Alfa) dissolved in 18 cc water. The zeolite was mixed in a dish during impregnation, and allowed to sit 29 minutes, then dried 61 minutes at 100° C. in a vacuum oven. The product was G1 in Table 3.

33.52 g of G1 was placed in a vycor tube in an upright furnace. Over a period of 23 minutes, the furnace was heated to 550° C. under flowing nitrogen. After 1 hour, the furnace was cooled to 500° C.; the nitrogen flow was stopped and an air flow was begun. After 30 minutes, the furnace was turned off, the air was stopped, nitrogen flow was restarted, nd the tube was allowed to cool. The product was G2 in Table 3.

12.01 g of G2 was impregnated with 5.50 g potassium carbonate dissolved in 6 cc water. The zeolite was mixed in a dish during impregnation, allowed to sit 49 minutes, then dried 64 minutes at 100° C. in a vacuum oven. The result was G3.

The dried material was placed in a vycor tube in an upright furnace. With nitrogen flowing, the furnace was heated to 550° C. After 1 hour, the furnace was turned off and the tube allowed to cool, while still under flowing nitrogen. The product was material G4 of Table 3.

EXAMPLE L

Impregnation With Alcoholic Solution 30.73 g K-L zeolite was stirred with 300 cc Barnstead deionized water. After 1 hour of stirring, the mixture was filtered an additional 200 cc water was poured through the funnel. The paste was dried 1 hour at 150±C in a vacuum oven.

12.61 g washed K-L was impregnated with 3.13 g potassium methoxide dissolved in 8 cc methanol. The zeolite was mixed in a dish during impregnation, allowed to sit 15 minutes, then dried 16 hours at 150° C. in a vacuum oven. The result was F33 in Table 3.

The material F33 was placed in a vycor tube in an upright furnace. The nitrogen flow rate was set at 250 cc/min and the furnace was heated to 200° C. over a period of 6 minutes. After 25 minutes, the furnace temperature was increased to 550° C. After 2 hours, the furnace was turned off and allowed to cool, while still under flowing nitrogen. The product was material F34 in Table 3.

EXAMPLE M

Impregnation With Non Hydroxylic Solution 5.04 g washed NaY zeolite (washed as in Example I) was impregnated with 1.04 g lithium acetate dissolved in 3 cc dimethylsulfoxide. The zeolite was mixed in a dish during impregnation, allowed to sit 10 minutes, then dried 18 hours and 19 minutes in a 200° C. vacuum oven. The result was material F37.

The dried material F37 was placed in a vycor tube in an upright furnace. The nitrogen flow rate was set at 225 cc/min and the furnace was heated to 200° C. over a period of 10 minutes. After 40 minutes, the furnace temperature was raised to 550° C. After 2 hours at 550° C.; the furnace was turned off and the tube allowed to cool while still under flowing nitrogen. The resulting product was material F38 of Table 3.

TABLE 3

Illustrative Embodiments, part A

| Description #: CATALYST & System & Designation & (Salt/Zeolite) | Materials used | | | | Conditions | | | Structure | | n-C$_8$ wetness cc/g$^{f)}$ |
|---|---|---|---|---|---|---|---|---|---|---|
| | Solvent | Solv. Wt. | Salt Wt. | Zeol. Wt. | Temp.$^{a)}$ | Method$^{b)}$ | Example$^{c)}$ | XRD % xtal$^{d)}$ | S.A. sq. m./g$^{e)}$ | |
| Reference materials: | | | | | | | | | | |
| KOH pellets | — | — | — | — | — | — | — | — | — | — |
| Shell Silica Spheres | — | — | — | — | — | — | — | — | — | — |
| Sodium Amide | — | — | — | — | — | — | — | — | — | — |
| NaY$_+$ washed | — | — | — | — | 150 | — | — | 100 | — | — |
| NH$_4$ Mordenite | — | — | — | — | — | — | — | 100 | — | — |
| Na Mordenite | — | — | — | — | — | — | — | 97.2 | — | — |
| Water (Barnstead 20 Mohm) | — | — | — | — | — | — | — | — | — | — |
| MgO | — | — | — | — | — | — | — | — | — | — |
| LiOH | — | — | — | — | — | — | — | — | — | — |
| K/L zeolite | — | — | — | — | — | — | — | — | — | — |
| LZY82 pellets | — | — | — | — | — | — | — | 60.8 | 556 | — |
| LZY62 pellets | — | — | — | — | — | — | — | — | 670+ | — |
| LZY52 pellets | — | — | — | — | — | — | — | — | 825+ | — |
| LZY82 powder | — | — | — | — | — | — | — | — | 770+ | — |
| SDUSY | — | — | — | — | — | — | — | — | — | — |
| Natural Erionite | — | — | — | — | 150 | — | — | — | — | — |
| Natural Mordenite | — | — | — | — | 150 | — | — | — | — | — |
| Natural Chabazite | — | — | — | — | 150 | — | — | — | — | — |
| NaX | — | — | — | — | — | — | — | — | — | — |
| 4A | — | — | — | — | — | — | — | — | — | — |
| 5A | — | — | — | — | — | — | — | — | — | — |
| K methoxide | — | — | — | — | — | — | — | — | — | — |
| K$_2$CO$_3$ | — | — | — | — | — | — | — | — | — | — |
| K oxalate | — | — | — | — | — | — | — | — | — | — |
| KNO$_3$ | — | — | — | — | — | — | — | — | — | — |
| K acetate | — | — | — | — | — | — | — | — | — | — |
| Cs acetate | — | — | — | — | — | — | — | — | — | — |
| Li acetate | — | — | — | — | — | — | — | — | — | — |
| Illustrative Embodiments of Basic Zeolites: | | | | | | | | | | |
| A1  K$_2$CO$_3$/NaY | H$_2$O | 25 | 1.9 | 50.01 | 100 | I | A | 105 | — | 1.5 |
| A2  K$_2$CO$_3$/NaY | Same as A1, | | calcined | | 460 | I | B | 110 | — | 1.5 |
| A3  K$_2$CO$_3$/NaY | Same as A1, | | calcined | | 250 | I | B | 107 | — | 1.47 |
| A4  K$_2$CO$_3$/NaY | Same as A1, | | calcined | | 350 | I | B | 108 | — | 1.51 |

| Description #: CATALYST & System & Designation & (Salt/Zeolite) | Structure Pore vol cc/g$^{g)}$ | Basicity Resulting | | | |
|---|---|---|---|---|---|
| | | pH 1% aq.$^{h)}$ | INDICATOR COLORS (i) | | |
| | | | 4-nitro-aniline/DMSO | 4-chloro aniline/DMSO | 4-nitro-aniline/benzene | 4-chloro-aniline/benzene |
| Reference materials: | | | | | | |
| KOH pellets | — | 14 | blue | beige | pinkish/lavender | creme |
| Shell Silica Spheres | — | 6 | yellow | beige | yellow | creme |
| Sodium Amide | — | 14 | dk blue | olive drab | dk blue | purp/bwn |
| NaY$_+$ washed | — | 6 | yellow | nd | nd | cream |
| NH$_4$ Mordenite | — | 6 | yellow | nd | nd | cream |
| Na Mordenite | — | 7 | yellow | nd | nd | cream |
| Water (Barnstead 20 Mohm) | — | 6 | — | — | — | — |
| MgO | — | 10 | yellow | nd | nd | cream |
| LiOH | — | 13 | green | nd | nd | cream |
| K/L zeolite | — | 7 | lt lime grn | nd | nd | white |
| LZY82 pellets$^{j),p)}$ | .396 | 6 | yellow | nd | nd | cream |
| LZY62 pellets | — | 5 | yellow | nd | nd | cream |
| LZY52 pellets | — | 6 | yellow/grn | nd | nd | cream |
| LZY82 powder | — | 6 | yellow | nd | nd | cream |
| SDUSY$^{q)}$ | — | 6 | yellow | nd | nd | cream |
| Natural Erionite | — | 6 | golden | nd | nd | sl orng |
| Natural Mordenite | — | 6 | golden | nd | nd | cream |
| Natural Chabazite | — | 7 | yellow | nd | nd | cream |

TABLE 3-continued

Illustrative Embodiments, part A

| | | | | | | |
|---|---|---|---|---|---|---|
| NaX | — | 7 | yellow | nd | nd | cream |
| 4A | — | 7 | yellow | nd | nd | cream |
| 5A | — | 7 | yellow | nd | nd | cream |
| K methoxide | — | 14 | dk brown | nd | nd | off-white |
| $K_2CO_3$ | — | 11 | dk green | | | cream |
| K oxalate | — | 7 | yellow | nd | nd | cream |
| $KNO_3$ | — | 6 | yellow | nd | nd | cream |
| K acetate | — | 7 | yellow | nd | nd | cream |
| Cs acetate | — | 7 | yellow/grn | nd | nd | cream |
| Li acetate | — | 8 | green | nd | nd | cream |
| Illustrative Embodiments of Basic Zeolites: | | | | | | |
| A1 $K_2CO_3$/NaY | — | — | dk green | cream | sl orng yell | cream |
| A2 $K_2CO_3$/NaY | — | — | dk blue | lt beige | muddy grn/orng | lt pink |
| A3 $K_2CO_3$/NaY | — | — | dk blue | lt beige | orng/yell | cream |
| A4 $K_2CO_3$/NaY | — | — | dk green | lt beige | sl bwn in orng/yell | cream |

Footnotes:
a) Maximum temperature used in drying (calcining) the particular material, in degrees Centigrade.
b) General method of preparation. I=Impregnation S=Slurry (Exchange in a wash of salt solution) M=impregnation with molten salt.
c) Closest example described in text above, by code letter.
d) Per cent crystallinity by X-ray diffraction comparison to best available standard sample material by ASTM D3906-80 for faujasites, and a modification of this method for the other zeolites.
e) Surface area in square meters/gram by nitrogen absorption, via the two point surface area method on a Micromeritics Digisorb 2500 Instrument (Digisorb is a trademark of Micromeritics Corporation) using the Micromitics program table for this machine.
f) Amount of n-octane, cc/g, necessary to make the catalyst powder appear moist.
g) Pore volume in cubic centimeters per gram, determined by nitrogen absorption via the equipment described in e) except where provided by the manufacturer (+).
h) pH of a one percent suspension of the catalyst in deionized (Barnstead, 20 meg ohm) water, read with pH paper after 20 minutes.
i) Color of a suspension of about 60mg of catalyst in about 0.1 cc of a 10% weight solution of the indicator solution listed, by a modification of the method of Tanabe (in Solid Acids and Bases, Academic Press, 1970). The leftmost system probably indicates pH of about 16 or more, while the rightmost system should indicate pH of 27 or more, according to Tanabe. (orng=orange, orangish;yell=yellow; grn=green, greenish;dk=dark;bwn=brown, brownish; lt=light;sl=slight; ex=extremely;dp=deep;w/=with;nd=not determined;liq=liquid).
j) KOAc=potassium acetate;CsOAc=cesium acetate; LZY—plt-=Linde zeolite Y type—pellets from Union Carbide Corp.; 4A=-sodium zeolite A type —from Aldrich; 5A=calcium zeolite A type—from Davison.
k) "I"=impregnation with pure water followed by drying to redistribute the loading of salt previously impregnated, as in method G.
l) WshNaMord=washed Na mordenite, thoroughly washed with purified Barnstead water until pH of solid is constant at 6.
m) LZY82pwdr=hydrostatically pressed (20,000 to 30,000 psi) and sieved 16-30 mesh powder.
n) The molten salt was impregnated into the washed NaY zeolite at 200 degrees Centigrade to 220 degrees Centigrade.
o) Black due to the color of ruthenium. Note color changes with other metals and the ability of the indicator to shade and bury the metal species' color.
p) Pellet contain approximately 20% $Al_2O_3$.
q) Super Dealuminated USY; $SiO_2/Al_2O_3 \sim 25$.

TABLE 3

Illustrative Embodiments, Part B.
(Footnotes are those of Part A)

| Description #: CATALYST & System & Designation & (Salt/Zeolite) | Materials used | | | | Conditions | | | Structure | | n-C$_8$ wetness cc/g[f] |
|---|---|---|---|---|---|---|---|---|---|---|
| | Solvent | Solv. Wt. | Salt Wt. | Zeol. Wt. | Temp.[a] | Method[b] | Example[c] | XRD% xtal[d] | S.A. sq. m./g[e] | |
| B1 $K_2CO_3$/NaY | $H_2O$ | 25 | 15 | 25.39 | 100 | I | C | 33 | — | — |
| B2 $K_2CO_3$/NaY | | (same as A1) | | | 250 | I | B | 75 | — | — |
| B3 $K_2CO_3$/NaY | | (same as A1) | | | 450 | I | B | 78 | — | — |
| B4 $K_2CO_3$/NaY | | (same as B1) | | | 250 | I | C | 19 | — | — |
| B5 $K_2CO_3$/NaY | | (same as B1) | | | 450 | I | C | 11 | — | — |
| B6 $Na_2CO_3$/4A[j] | $H_2O$ | 10 | 4.53 | 20.02 | 70 | I | C | — | — | — |
| B7 $Na_2CO_3$/4A | | (same as B6) | | | 450 | I | C | — | — | — |
| B8 $K_2CO_3$/NaY | $H_2O$ | 50 | 3.84 | 100.5 | 100 | I | A | 84 | — | — |
| B9 $K_2CO_3$/NaY | $H_2O$ | 75 | 5.76 | 150 | 100 | I | A | 88.4 | — | — |
| B10 $K_2CO_3$/NaY | $H_2O$ | 61 | 36.53 | 61.7 | 100 | I | C | 40 | — | — |
| B11 $K_2CO_3$/5A[j] | $H_2O$ | 60 | 45.53 | 100 | 500 | I | C | — | — | — |
| B12 KOH/NaY | $H_2O$ | 6000 | 168 | 50.6 | 100 | S | D | — | — | — |
| B13 KOH/NaY | $H_2O$ | 3000 | 168 | 50.4 | 100 | S | D | — | — | — |
| B14 $K_2CO_3$/NaY | $H_2O$ | 50 | 45.6 | 100 | 100 | I | C | 89.5 | — | — |
| B15 $K_2CO_3$/NaY | $H_2O$ | | (same as B14) | | 550 | I | C | 89.3 | — | — |
| B16 $NaNO_3$/$NH_4$-USY | $H_2O$ | 1000 | 171 | 101 | — | S | E | | | |
| | $H_2O$ | 1000 | 0 | 101 | — | wash | | | | |
| | $H_2O$ | 1000 | 171 | 101 | — | S | | | | |
| | $H_2O$ | 1000 | 0 | 101 | 100 | wash | | — | 757 | — |
| B17 $KNO_3$/NaY | $H_2O$ | 20 | 16.64 | 50.8 | 100 | I | C | 67.1 | — | — |
| B18 $KNO_3$/NaY | $H_2O$ | | (same as B17) | | 550 | I | C | 56.2 | — | — |
| B19 KOH/NaY | $H_2O$ | 20 | 20.1 | 50 | 100 | I | C | 11.4 | — | — |
| B20 KOH/NaY | $H_2O$ | | (same as B19) | | 550 | I | C | 0 | — | — |
| B21 KOH/NaY | $H_2O$ | 20 | 2.12 | 50 | 100 | I | A | 84.3 | — | — |
| B22 KOH/NaY | $H_2O$ | | (same as B21) | | 550 | I | A | 87.9 | — | — |
| B23 K oxalate/NaY | $H_2O$ | 70 | 23.4 | 50 | 100 | I | C | 37.3 | — | — |
| B24 K oxalate/NaY | $H_2O$ | | (same as B23) | | 550 | I | C | 9 | — | — |

| Description #: CATALYST & System & Designation & (Salt/Zeolite) | Structure | | | Basicity Resulting | | | |
|---|---|---|---|---|---|---|---|
| | Cond- itions cc/g[g] | Pore vol Temp.[a] | pH 1% aq.[h] | INDICATOR COLORS (i) | | | |
| | | | | 4-nitro- aniline/DMSO | 4-chloro- aniline/DMSO | 4-nitro- aniline/benzene | 4-chloro- aniline/benzene |
| B1 $K_2CO_3$/NaY | 100 | — | 11 | Kelly grn | cream | dirty yell | cream |

TABLE 3-continued

Illustrative Embodiments, Part B.
(Footnotes are those of Part A)

| | | | | | | | | |
|---|---|---|---|---|---|---|---|---|
| B2 | K$_2$CO$_3$/NaY | 250 | — | 9 | Blue grn | lt pink | orange | cream |
| B3 | K$_2$CO$_3$/NaY | 450 | — | 8 | dp blue grn | amber | yell bwn | cream |
| B4 | K$_2$CO$_3$/NaY | 250 | — | — | ex dp blue green | amber | olive drab | cream |
| B5 | K$_2$CO$_3$/NaY | 450 | — | 9 | dp blue/dp green | lt pink | opaque blackish grn | cream |
| B6 | Na$_2$CO$_3$/4A | | 70 | — | | | | |
| B7 | Na$_2$CO$_3$/4A | 450 | — | — | | | | |
| B8 | K$_2$CO$_3$/NaY | 100 | — | 10 | green | nd | nd | white |
| B9 | K$_2$CO$_3$/NaY | 100 | — | 10 | dk lime grn | nd | nd | white |
| B10 | K$_2$CO$_3$/NaY | 100 | — | 11 | dk grn blue | nd | nd | white |
| B11 | K$_2$CO$_3$/5A | 500 | — | — | | | | |
| B12 | KOH/NaY | 100 | — | 9.5 | green | nd | nd | white |
| B13 | KOH/NaY | 100 | — | 8 | dk green | nd | nd | white |
| B14 | K$_2$CO$_3$/NaY | 100 | — | 10 | dk green | nd | nd | white |
| B15 | K$_2$CO$_3$/NaY | 550 | — | 10 | nd | nd | nd | nd |
| B16 | NaNO$_3$/NH$_4$-USY | — | | | | | | |
| | | — | | | | | | |
| | | 100 | — | 7 | yellow | nd | nd | white |
| B17 | KNO$_3$/NaY | 100 | — | 7 | yellow | nd | nd | cream |
| B18 | KNO$_3$/NaY | 550 | — | 7 | lt yell grn | nd | nd | lt pink |
| B19 | KOH/NaY | 100 | — | 12 | | | | |
| B20 | KOH/NaY | 550 | — | 11 | dk blue grn | nd | nd | dk cream |
| B21 | KOH/NaY | 100 | — | 9 | | | | |
| B22 | KOH/NaY | 550 | — | 10 | very dk grn; blue green | nd | nd | lt amber w/ sl lavender |
| B23 | K oxalate/NaY | 100 | — | 8 | | | | |
| B24 | K oxalate/NaY | 550 | — | 11 | very dk grn solid; blue liq | nd | nd | purple & gray |

TABLE 3

Illustrative Embodiments, Part C.
(Footnotes are those of Part A)

| Description #: CATALYST & System & Designation & (Salt/Zeolite) | Materials used | | | | Conditions | | | Structure | | n-C$_8$ wetness cc/g$^{f)}$ |
|---|---|---|---|---|---|---|---|---|---|---|
| | Solvent | Solv. Wt. | Salt Wt. | Zeol. Wt. | Temp.$^{a)}$ | Method$^{b)}$ | Example$^{c)}$ | XRD% xtal$^{d)}$ | S.A. sq. m./g$^{e)}$ | |
| C1 | K$_2$CO$_3$/NaY | H$_2$O | 10 | 11.6 | 24.9 | 100 | I | C | 37.4 | 129 | — |
| C2 | K$_2$CO$_3$/NaY | H$_2$O | (same as C1) | | | 550 | I | C | 12 | 74 | — |
| C3 | K$_2$CO$_3$/NaY | H$_2$O | 14 | 4.02 | 25 | 580 | I | C | 1 | 38 | — |
| C4 | K acetate/NaY | H$_2$O | 300 | 29.8 | 10 | 100 | S | D | — | — | — |
| C5 | K acetate/NaY | H$_2$O | (same as C4) | | | 550 | S | D | 16 | — | — |
| C6 | K acetate/NaY | H$_2$O | 4 | 0.12 | 10.1 | 100 | I | A | | | |
| C7 | K acetate/NaY | H$_2$O | (same as C6) | | | 550 | I | A | 96 | — | — |
| C8 | K acetate/NaY | H$_2$O | 4 | 0.22 | 10.1 | 100 | I | A | | | |
| C9 | K acetate/NaY | H$_2$O | (same as C8) | | | 550 | I | A | 97 | | |
| C10 | K acetate/NaY | H$_2$O | 4 | 1.2 | 10 | 100 | I | C | | | |
| C11 | K acetate/NaY | H$_2$O | (same as C10) | | | 550 | I | C | 37 | — | — |
| C12 | K acetate/NaY | H$_2$O | 4 | 2.02 | 10 | 100 | I | C | | | |
| C13 | K acetate/NaY | H$_2$ | (same as C12) | | | 550 | I | C | 15 | — | — |
| C14 | K acetate/KL | H$_2$O | 10 | 22.1 | 20 | 100 | I | C | | | |
| C15 | K acetate/KL | | (as above) | | | 550 | I | C | 29 | 74 | |
| C16 | K acetate/KL | H$_2$O | 10 | 3.35 | 20.1 | 100 | I | C | | | |
| C17 | K acetate/KL | H$_2$O | (as C16) | | | 550 | I | C | 81 | — | — |
| C18 | KOAc/LZY82plt(j) | H$_2$O | 3.4 | 8.6 | 21.2 | 100 | I | C | 31 | 145 | — |
| C19 | KOAc/LZY82plt | H$_2$O | (as C18) | | | 550 | I | C | 14 | 135 | — |
| C20 | CsOAc/LZY82plt | H$_2$O | 400 | 76.4 | 20.2 | 100 | S | D | 24 | 371 | — |
| C21 | CsOAc/LZY82plt | H$_2$O | 1.8 | 1.82 | 20 | 100 | I/S | E | 32 | 347 | — |
| C22 | CsOAc/LZY82plt | H$_2$O | (sample above) | | | 550 | I/S | E | 24 | 370 | — |
| C23 | CsOAc/LZY52plt | H$_2$O | 0.74 | 1.48 | 2.04 | 550 | I | F | 21 | — | — |
| C24 | KOAc/LZY52plt | H$_2$O | 0.34 | 0.70 | 2.08 | 550 | I | F | 42 | — | — |
| C25 | KOAc/LZY82plt | H$_2$O | 0.67 | 1.37 | 2.02 | 550 | I | F | 3 | — | — |
| C26 | CsOAc/LZY62plt | H$_2$O | 0.72 | 1.43 | 2.01 | 550 | I | F | 11.2 | — | — |
| C27 | CsOAc/LZY62plt | H$_2$O | 1.02 | 2.04 | 2.00 | 550 | I | F | 7.1 | — | — |
| C28 | KOAc/LZY62plt | H$_2$O | 0.33 | 0.68 | 2.07 | 550 | I | F | 27.4 | — | — |

| Description #: CATALYST & System & Designation & (Salt/Zeolite) | Cond- itions Temp.$^{a)}$ | Structure Pore vol cc/g$^{g)}$ | pH 1% aq.$^{h)}$ | Basicity Resulting INDICATOR COLORS (i) | | | |
|---|---|---|---|---|---|---|---|
| | | | | 4-nitro- aniline/DMSO | 4-chloro- aniline/DMSO | 4-nitro- aniline/benzene | 4-chloro- aniline/benzene |
| C1 | K$_2$CO$_3$/NaY | 100 | 0.1 | 11 | | | | |
| C2 | K$_2$CO$_3$/NaY | 550 | 0.06 | 11 | very dk grn | nd | nd | amber |
| C3 | K$_2$CO$_3$/NaY | 580 | 0.05 | 10 | dk green | nd | nd | purple solid amber liq. |
| C4 | K acetate/NaY | 100 | — | 7 | | | | |

TABLE 3-continued
Illustrative Embodiments, Part C.
(Footnotes are those of Part A)

| | | | | | | | | |
|---|---|---|---|---|---|---|---|---|
| C5 | K acetate/NaY | 550 | — | 8 | dk kelly grn | nd | nd | dark |
| C6 | K acetate/NaY | 100 | | 9 | | | | |
| C7 | K acetate/NaY | 550 | — | 9 | dk kelly grn | nd | nd | dk purple bwn |
| C8 | K acetate/NaY | 100 | | 9 | | | | |
| C9 | K acetate/NaY | 550 | — | 9 | dk kelly grn | nd | nd | dk purple bwn |
| C10 | K acetate/NaY | 100 | | 10 | | | | |
| C11 | K acetate/NaY | 550 | — | 9 | dk kelly grn | nd | nd | very dark |
| C12 | K acetate/NaY | 100 | | 10 | | | | |
| C13 | K acetate/NaY | 550 | — | 9 | dk kelly grn | nd | nd | black |
| C14 | K acetate/KL | 100 | | | | | | |
| C15 | K acetate/KL | 550 | 0.04 | 12 | deep green | nd | nd | black |
| C16 | K acetate/KL | 100 | | | | | | |
| C17 | K acetate/KL | 550 | 0.06 | 11 | deep green | nd | nd | black |
| C18 | KOAc/LZY82plt(j) | 100 | 0.17 | | | | | |
| C19 | KOAc/LZY82plt | 550 | 0.17 | 10 | dk green | nd | nd | black |
| C20 | CsOAc/LZY82plt | 100 | 0.3 | | | | | |
| C21 | CsOAc/LZY82plt | 100 | 0.28 | | | | | |
| C22 | CsOAc/LZY82plt | 550 | 0.3 | 7 | dk grn/yell liq | nd | nd | beige/bwn |
| C23 | CsOAc/LZY52plt | 550 | — | 10 | dk green | nd | nd | beige |
| C24 | KOAc/LZY52plt | 550 | — | 9 | dk kelly green liquid | nd | nd | dark;clear dk grn & white |
| C26 | CsOAc/LZY62plt | 550 | — | 9 | dk plts;kelly green liq | nd | nd | lt gray plt amber liq |
| C27 | CsOAc/LZY62plt | 550 | — | 9 | dk plts;kelly green liq | nd | nd | lt gray plt amber liq |
| C28 | KOAc/LZY62plt | 550 | — | 9 | black/blue grn liq | nd | nd | dark/amber liq |

TABLE 3
Illustrative Embodiments, Part D.
(Footnotes are those of Part A)

| Description #: CATALYST & System & Designation & (Salt/Zeolite) | Materials used | | | | Conditions | | | Structure | | n-C$_8$ wetness cc/g$^f$ |
|---|---|---|---|---|---|---|---|---|---|---|
| | Solvent | Solv. Wt. | Salt Wt. | Zeol. Wt. | Temp.$^a$ | Method$^b$ | Example$^c$ | XRD% xtal$^d$ | S.A. sq. m./g$^e$ | |
| D1 | KOAc/LZY62plts | H$_2$O | 0.52 | 1.06 | 2.07 | 550 | I | F | 16.2 | — | — |
| D2 | KOAc/LZY62plts | H$_2$O | 0.68 | 1.39 | 2.03 | 550 | I | F | 8 | — | — |
| D3 | CsOAc/LZY82plts | H$_2$O | 0.67 | 1.33 | 2.03 | 550 | I | F | 15 | — | — |
| D4 | KOAc/LZY82plts | H$_2$O | 0.50 | 1.03 | 2.04 | 550 | I | F | 7 | — | — |
| D5 | KOAc/LZY82plts | H$_2$O | 0.33 | 0.67 | 2.01 | 550 | I | F | 28.4 | — | — |
| D6 | K$_2$CO$_3$/Erionite | H$_2$O | 0.5 | 0.51 | 1.04 | 150 | I | F | | | |
| | | H$_2$O | 2×0.65 | 0 | above | 150 | "I"(k) | G | | | |
| | | | | | above | 550 | | G | 20 | — | — |
| D7 | K oxalate/Erion. | H$_2$O | 1.53 | 0.49 | 1.05 | 150 | I | C | | | |
| | | H$_2$O | 2×0.6 | 0 | above | 150 | "I" | G | | | |
| | | | | | above | 550 | | G | 43 | — | — |
| D8 | K$_2$CO$_3$/Mordenite | H$_2$O | 1.02 | 1.02 | 1.99 | 150 | I | C | | | |
| | | H$_2$O | 2×0.6 | 0 | above | 150 | "I" | G | | | |
| | | | | | above | 550 | | G | 33 | — | — |
| D9 | K oxalate/Mord. | H$_2$O | 3.05 | 0.98 | 2.05 | 150 | I | C | | | |
| | | H$_2$O | 2×1.5 | 0 | above | 150 | "I" | G | | | |
| | | | | | above | 550 | | G | 46.4 | — | — |
| D10 | K$_2$CO$_3$/Chabazite | H$_2$O | 0.05 | 0.06 | 010 | 150 | I | C | | | |
| | | H$_2$O | 2×0.05 | 0 | above | 150 | "I" | G | | | |
| | | | | | above | 550 | | G | 14.4 | — | — |
| D11 | K oxalate/Chab. | H$_2$O | 0.15 | 0.05 | 0.10 | 150 | I | C | | | |
| | | H$_2$O | 2×0.05 | 0 | above | 150 | "I" | G | | | |
| | | | | | above | 550 | | G | 18 | — | — |
| D12 | CsOAc/Mordenite | H$_2$O | 0.33 | 0.67 | 2.03 | 150 | I | C | | | |
| | | H$_2$O | 1.00 | 0 | above | 150 | "I" | G | | | |
| D13 | CsOAc/Mordenite | | | | above | 550 | | G | 45 | — | — |
| D14 | CsOAc/Erionite | H$_2$O | 0.06 | 0.13 | 0.33 | 150 | I | C | | | |
| | | H$_2$O | 0.2 | 0 | above | 150 | "I" | G | | | |
| | | | | | above | 550 | | G | 38 | — | — |

| Description #: CATALYST & System & Designation & (Salt/Zeolite) | Structure Conditions Temp.$^a$ | Pore vol cc/g$^g$ | Basicity Resulting | | | | |
|---|---|---|---|---|---|---|---|
| | | | pH 1% aq.$^h$ | 4-nitro-aniline/DMSO | 4-chloro-aniline/DMSO | 4-nitro-aniline/benzene | 4-chloro-aniline/benzene |
| D1 | KOAc/LZY62plts | 550 | — | 9 | dp blue grn | nd | nd | dk/amber liq |
| D2 | KOAc/LZY62plts | 550 | — | 9 | dk/dp blue grn | nd | nd | dk/amber liq |
| D3 | CsOAc/LZY82plts | 550 | — | 9 | dk/kelly grn | nd | nd | dk grn/amber liq |
| D4 | KOAc/LZY82plts | 550 | — | 9 | dk grn/lime grn/liq | nd | nd | dk/amber liq |
| D5 | KOAc/LZY82plts | 550 | — | 8 | dk/lime grn liq | nd | nd | dk bwn/clear |

TABLE 3-continued

Illustrative Embodiments, Part D.
(Footnotes are those of Part A)

| | | | | | | | | |
|---|---|---|---|---|---|---|---|---|
| D6 | $K_2CO_3$/Erionite | 150 | | | | | | |
| | | 150 | | | | | | |
| | | 550 | — | 12 | dk green | nd | nd | lt bwn/amber |
| D7 | K oxalate/Erion. | 150 | | | | | | |
| | | 150 | | | | | | |
| | | 550 | — | 11 | dk green | nd | nd | dk bwn/amber |
| D8 | $K_2CO_3$Mordenite | 150 | | | | | | |
| | | 150 | | | | | | |
| | | 550 | — | 12 | dk green | nd | nd | bwn/clear liq |
| D9 | K oxalate/Mord. | 150 | | | | | | |
| | | 150 | | | | | | |
| | | 550 | — | 12 | dk green | nd | nd | bwn/lavender |
| D10 | $K_2CO_3$/Chabazite | 150 | | | | | | |
| | | 150 | | | | | | |
| | | 550 | — | 11 | green | nd | nd | white/clear |
| D11 | K oxalate/Chab. | 150 | | | | | | |
| | | 150 | | | | | | |
| | | 550 | — | 11 | green/yell | nd | nd | dk/clear |
| D12 | CsOAc/Mordenite | 150 | | | | | | |
| | | 150 | | | | | | |
| D13 | CsOAc/Mordenite | 550 | — | 9 | blue green | nd | nd | purple/amber |
| D14 | CsOAc/Erionite | 150 | | | | | | |
| | | 150 | | | | | | |
| | | 550 | — | 7 | blue green lavender liq | nd | nd | dp purple/ lavender liq |

TABLE 3

Illustrative Embodiments, Part E.
(Footnotes are those of Part A)

| Description #: CATALYST & System & Designation & (Salt/Zeolite) | | Materials used | | | Conditions | | | Structure | | |
|---|---|---|---|---|---|---|---|---|---|---|
| | Solvent | Solv. Wt. | Salt Wt. | Zeol. Wt. | Temp.[a] | Method[b] | Example[c] | XRD% xtal[d] | S.A. sq. m./g[e] | n-$C_8$ wetness cc/g[f] |
| E1 | $K_2CO_3$/NaMord. | $H_2O$ | 0.5 | 0.5 | 4.08 | 150 | I | C | | | |
| | | $H_2O$ | 1.0 | 0 | above | 150 | "I" | G | | | |
| | | | above | | | 550 | | G | 42 | — | — |
| E2 | K oxalate/NaMord | $H_2O$ | 0.75 | 0.24 | 4.06 | 150 | I | C | | | |
| | | $H_2O$ | 1.0 | 0 | above | 150 | "I" | G | | | |
| | | | above | | | 550 | | G | 75 | — | — |
| E3 | LiOAc/NaMord. | $H_2O$ | 0.51 | 0.49 | 4.06 | 150 | I | C | | | |
| | | $H_2O$ | 1.0 | 0 | above | 150 | "I" | G | | | |
| | | | above | | | 550 | | G | 46 | — | — |
| E4 | CsOAc/NaMord. | $H_2O$ | 0.33 | 0.67 | 4.06 | 150 | I | C | | | |
| | | $H_2O$ | 1.0 | 0 | above | 150 | "I" | G | | | |
| | | | above | | | 550 | | G | 50 | — | — |
| E5 | $K_2CO_3$/wshNaMord (l) | $H_2O$ | 0.5 | 0.5 | 4.01 | 150 | I | C | | | |
| | | $H_2O$ | 1.0 | 0 | above | 150 | "I" | G | | | |
| | | | above | | | 550 | | G | 64 | — | — |
| E6 | Koxalate/wshNaM. | $H_2O$ | 0.75 | 0.24 | 4.06 | 150 | I | C | | | |
| | | $H_2O$ | 1.0 | 0 | above | 150 | "I" | G | | | |
| | | | above | | | 550 | | G | 83 | — | — |
| E7 | KOAc/wshNaMord | $H_2O$ | 0.33 | 0.67 | 4.04 | 150 | I | C | | | |
| | | $H_2O$ | 1.0 | 0 | above | 150 | "I" | G | | | |
| | | | above | | | 550 | | G | 31 | — | — |
| E8 | LiOAc/wshNaMord | $H_2O$ | 0.51 | 0.49 | 4.03 | 150 | I | C | | | |
| | | $H_2O$ | 1.0 | 0 | above | 150 | "I" | G | | | |
| | | | above | | | 550 | | G | 50.4 | — | — |
| E9 | $K_2CO_3$/$NH_4$Morden | $H_2O$ | 40/2 | Molar | 4.01 | 23 | S | H | | | |
| | | $H_2O$ | 2×50 | 0 | above | 150 | Wash | H | — | — | — |
| | | $H_2O$ | 40/2 | Molar | above | 23 | S | H | | | |
| | | $H_2O$ | 2×50 | 0 | above | 23 | Wash | H | — | — | — |
| | | | above | | | 150 | | H | | | |
| E10 | $K_2CO_3$/LZY82pwdr (m) | $H_2O$ | 40/2 | Molar | 4.03 | 23 | S | H | | | |
| | | $H_2O$ | 2×50 | 0 | above | 150 | Wash | H | — | — | — |
| | | $H_2O$ | 40/2 | Molar | above | 23 | S | H | | | |
| | | $H_2O$ | 2×50 | 0 | above | 23 | Wash | H | — | — | — |
| | | | above | | | 150 | | H | | | |

| Description #: CATALYST & System & Designation & (Salt/Zeolite) | Structure Conditions cc/g[g] | Pore vol Temp.[a] | Basicity Resulting pH 1% aq.[h] | INDICATOR COLORS (i) | | | |
|---|---|---|---|---|---|---|---|
| | | | | 4-nitro-aniline/DMSO | 4-chloro-aniline/DMSO | 4-nitro-aniline/benzene | 4-chloro-aniline/benzene |
| E1 | $K_2CO_3$/NaMord. | 550 | | | | | |
| | | 150 | | | | | |
| | | 550 | — | 9 | lt grn/yell | nd | nd | offwhite |
| E2 | K oxalate/NaMord | 150 | | | | | |

TABLE 3-continued

Illustrative Embodiments, Part E.
(Footnotes are those of Part A)

|    |                |     |    |     |                |    |    |                      |
|----|----------------|-----|----|-----|----------------|----|----|----------------------|
|    |                | 150 |    |     |                |    |    |                      |
|    |                | 550 | —  | 9   | lt grn/blue grn| nd | nd | offwhite             |
| E3 | LiOAc/NaMord.  | 150 |    |     |                |    |    |                      |
|    |                | 150 |    |     |                |    |    |                      |
|    |                | 550 | —  | 9   | green/golden   | nd | nd | dk purple            |
| E4 | CsOAc/NaMord.  | 150 |    |     |                |    |    |                      |
|    |                | 150 |    |     |                |    |    |                      |
|    |                | 550 | —  | 8   | dark green     | nd | nd | dk brown             |
| E5 | K2CO3/wshNaMord| 150 |    |     |                |    |    |                      |
|    | (l)            | 150 |    |     |                |    |    |                      |
|    |                | 550 | —  | 10  | lt green/yell  | nd | nd | cream                |
| E6 | Koxalate/wshNaM.| 150|    |     |                |    |    |                      |
|    |                | 150 |    |     |                |    |    |                      |
|    |                | 550 | —  | 7   | lime green     | nd | nd | white                |
| E7 | KOAc/wshNaMord | 150 |    |     |                |    |    |                      |
|    |                | 150 |    |     |                |    |    |                      |
|    |                | 550 | —  | 8   | blue green     | nd | nd | dk purple            |
| E8 | LiOAc/wshNaMord| 150 |    |     |                |    |    |                      |
|    |                | 150 |    |     |                |    |    |                      |
|    |                | 550 | —  | 7   | dk grn/yell    | nd | nd | dk purple w/lavender |
| E9 | K2CO3/NH4Morden| 23  |    |     |                |    |    |                      |
|    |                | 150 | —  | 8   |                |    |    |                      |
|    |                | 23  |    |     |                |    |    |                      |
|    |                | 23  | —  | 9   |                |    |    |                      |
|    |                | 150 | —  | 9   | dark green     | nd | nd | pink                 |
| E10| K2CO3/LZY82pwdr| 23  |    |     |                |    |    |                      |
|    | (m)            | 150 | —  | 8   |                |    |    |                      |
|    |                | 23  | —  | —   |                |    |    |                      |
|    |                | 23  | —  | 9   |                |    |    |                      |
|    |                | 150 | —  | 9   | green          | nd | nd | cream                |

TABLE 3

Illustrative Embodiments, Part F.
(Footnotes are those of Part A)

| Description #: CATALYST & System & Designation & (Salt/Zeolite) | Solvent | Materials used Solv. Wt. | Salt Wt. | Zeol. Wt. | Conditions Temp.$^{a)}$ | Method$^{b)}$ | Example$^{c)}$ | Structure XRD% xtal$^{d)}$ | S.A. sq. m./g$^{e)}$ | n-C8 wetness cc/g$^{f)}$ |
|---|---|---|---|---|---|---|---|---|---|---|
| F1  | CsOAc/wshNaY   | None  | 0          | 0.87  | 8.63     | 200(n) | M   | I | —   | — | — |
| F2  |                |       | above      |       |          | 550    | M   | I | 84  | — | — |
| F3  | K2CO3/wshNaY   | H2O   | 5.5        | 7.07  | 15.03    | 150    | I   | C |     |   |   |
|     |                |       | above      |       |          | 550    |     | C | 12  | — | — |
| F4  | K2CO3/LZY82pwdr| H2O   | 12.64      | 12.64 | 30.0     | 150    | M   | C |     |   |   |
| F5  |                | H2O   | 10         | 0     | above    | 150    | "I" | G |     |   |   |
| F6  |                |       | ½ above mat'l |    |          | 550    |     | G |     |   |   |
| F7  | other ½ of F5  | H2O   | 8          | 0     | ½ of F5  | 150    | "I" | J |     |   |   |
| F8  |                | H2O   | 2×5.0      | 0     | above    | 150    | "I" | J |     |   |   |
| F9  |                | H2O   | 5          | 0     | all F6   | 150    | J   | J |     |   |   |
| F10 |                |       | above mat'l |      |          |        | J   | J | —   | — | — |
| F11 | LiOAc/LZY82pwdr| H2O   | 22         | 20.75 | 30.0     | 150    | I   | C |     |   |   |
| F12 |                | H2O   | 10         | 0     | above    | 150    | "I" | G |     |   |   |
| F13 |                |       | ½ mat'l    |       |          | 550    |     | G |     |   |   |
| F14 |                | H2O   | 3×5.0      | 0     | ½ F12    | 150    | "I" | J |     |   |   |
| F15 |                | H2O   | 5.0        | 0     | all F13  | 150    | "I" | J |     |   |   |
| F16 |                |       | above      |       |          | 550    |     | J | —   | — | — |
| F17 | CsOAc/LZY82pwd | H2O   | 10.0       | 35    | 30.0     | 150    | I   | F |     |   |   |
| F18 |                | H2O   | 10         | 0     | above    | 150    | "I" | G |     |   |   |
| F19 |                |       | ½ of F18 used |    |          | 550    |     | G |     |   |   |
| F20 |                | H2O   | 3×5.0      | 0     | ½ F18    | 150    | "I" | J |     |   |   |
| F21 |                | H2O   | 10         | 0     | all F19  | 150    | "I" | J |     |   |   |
| F22 |                |       | above material |   |          | 550    |     | J | —   | — | — |
| F23 | NaOAc/LZY82pwd | H2O   | 31.8       | 15.03 | 30.0     | 150    | I   | C |     |   |   |
| F24 |                | H2O   | 10         | 0     | above    | 150    | "I" | G |     |   |   |
| F25 |                | H2O   | 3×5.0      | 0     | ½ of F24 | 150    | "I" | J | 115 | — | — |
| F26 |                |       | Other ½ of F24 |   |          | 550    |     | J | 43  | — | — |
| F27 |                | H2O   | 5          | 0     | above    | 150    | "I" | J |     |   |   |
| F28 |                |       | above material |   |          | 550    |     | J | 29  |   |   |
| F29 | LiOAc/wshNaY   | CH3OH | 6 cc       | 2.06  | 10.05    | 150    | I   | L | 121 |   |   |
| F30 |                |       | above material |   |          | 550    |     | L | 120 |   |   |
| F31 | CsOAc/wshNaY   | MeOH  | 8 cc       | 2.03  | 10.08    | 150    | I   | L | 51  |   |   |
| F32 |                |       | above material |   |          | 550    |     | L | 57  |   |   |
| F33 | MeOK/wshKL     | MeOH  | 8 cc       | 3.13  | 12.61    | 150    | I   | L | 46  |   |   |
| F34 |                |       | above material |   |          | 550    |     | L | 68  |   |   |
| F35 | CsOAc/wshNaY   | DMSO  | 5.5 cc     | 1.12  | 5.11     | 200    | I   | M | 50  |   |   |
| F36 |                |       | above material |   |          | 550    |     | M | 48  |   |   |

TABLE 3-continued

Illustrative Embodiments, Part F.
(Footnotes are those of Part A)

| F37 | LiOAc/wshNaY | DMSO | 4 cc | 1.04 | 5.04 | 200 | I | M | 110 | — | — |
| F38 | | | above material | | | 550 | | M | 98 | — | — |

| Description #: CATALYST & System & Designation & (Salt/Zeolite) | Structure Cond- itions Pore vol cc/g$^{g)}$ | Temp.$^{a)}$ | pH 1% aq.$^{h)}$ | Basicity Resulting INDICATOR COLORS (i) | | | |
|---|---|---|---|---|---|---|---|
| | | | | 4-nitro- aniline/DMSO | 4-chloro aniline/DMSO | 4-nitro- aniline/benzene | 4-chloro- aniline/benzene |
| F1 CsOAc/wshNaY | 200(n) | — | 6 | yellow | nd | nd | white |
| F2 | 550 | | 10 | Dark Green | nd | nd | pink/amber |
| F3 K$_2$CO$_3$/wshNaY | 150 | | | | | | |
| | 550 | — | 11 | Dark Green | nd | nd | dk purple bwn |
| F4 K$_2$CO$_3$LZY82pwdr | 150 | | | | | | |
| F5 | 150 | | | | | | |
| F6 | 550 | — | 10 | Dark Green | nd | nd | dark lavender |
| F7 other ½ of F5 | 150 | | | | | | |
| F8 | 150 | — | 11 | light green | nd | nd | white |
| F9 | 150 | | | | | | |
| F10 | 550 | — | 7 | Dark Green | nd | nd | lavender |
| F11 LiOAc/LZY82pwdr | 150 | | | | | | |
| F12 | 150 | | | | | | |
| F13 | 550 | — | 10 | Dark Green | nd | nd | dark brown |
| F14 | 150 | — | 8 | yellow | nd | nd | white |
| F15 | 150 | | | | | | |
| F16 | 550 | — | 9 | Dark Green | nd | nd | dark lavender |
| F17 CsOAc/LZY82pwd | 150 | | | | | | |
| F18 | 150 | | | | | | |
| F19 | 550 | — | 12 | Dark Green | nd | nd | dark lavender |
| F20 | 150 | — | 8 | light green | nd | nd | white |
| F21 | 150 | | | | | | |
| F22 | 550 | — | 11 | Dark Green | nd | nd | black |
| F23 NaOAc/LZY82pwd | 150 | | | | | | |
| F24 | 150 | | | | | | |
| F25 | 150 | — | 8 | yellow | nd | nd | cream |
| F26 | 550 | — | 11 | Dark Green | nd | nd | black |
| F27 | 150 | | | | | | |
| F28 | 550 | — | 8 | Dark Green | nd | nd | deep purple |
| F29 LiOAC/wshNaY | 150 | — | 8 | lime green | nd | nd | cream |
| F30 | 550 | — | 10 | lime green | nd | nd | lt lavender/specks dk purp |
| F31 CsOAc/wshNaY | 150 | — | 7 | yellow | nd | nd | cream |
| F32 | 550 | — | 11 | medium grn | nd | nd | lavender/dk pur |
| F33 MeOK/wshKL | 150 | — | 11 | medium grn | nd | nd | cream |
| F34 | 550 | — | 12 | dark green | nd | nd | lavender |
| F35 CsOAc/wshNaY | 200 | — | 6 | golden bwn | nd | nd | lt brown |
| F36 | 550 | — | 9 | dark green | nd | nd | lavender&pink |
| F37 LiOAc/wshNaY | 200 | — | 6 | golden | nd | nd | lt pink-bwn |
| F38 | 550 | — | 10 | dark olive | nd | nd | dark purple |

TABLE 3

Illustrative Embodiments, Part G.
(Footnotes are those of Part A)

Alkali metal basified zeolites containing catalytic metal centers:

| Description #: CATALYST & System & Designation & (Salt/Zeolite) | Materials used | | | | Conditions | | | Structure | | n-C$_8$ |
|---|---|---|---|---|---|---|---|---|---|---|
| | Sol- vent | Solv. Wt. | Salt Wt. | Zeol. Wt. | Temp.$^{a)}$ | Method$^{b)}$ | Example$^{c)}$ | XRD% xtal$^{d)}$ | S.A. sq. m./g$^{e)}$ | wetness cc/g$^{g)}$ |
| G1 Ru(NO)(NO$_3$)$_3$/NaY | H$_2$O | 18 | 5 | 31.15 | 100 | I | K | | | |
| G2 Ru(NO)(NO$_3$)$_3$/NaY | | material above | | | 550 | | K | 74 | 574 | — |
| G3 K$_2$CO$_3$/G2(Ru/NaY) | H$_2$O | 6 | 5.5 | 12 | 100 | I | K | | | |
| G4 | | material above | | | 550 | | K | 23 | 190 | — |
| G5 Cu(NO$_3$)$_2$/NaY | H$_2$O | 40 | 7.7 | 50 | 100 | I | K | 41.1 | — | — |
| G6 | | material above | | | 550 | | K | 5 | — | — |
| G7 K$_2$Co$_3$/(CuNaY) | H$_2$O | 14 | 12.74 | 28 | 100 | I | K | 45.1 | — | — |
| G8 | | material above | | | 550 | | K | 28 | — | — |
| G9 Fe(NO$_3$)$_3$/NaY | H$_2$O | 40 | 5.82 | 50 | 100 | I | K | — | — | — |
| G10 Fe/NaY | | material above | | | 550 | | K | 81 | — | — |
| G11 K$_2$Co$_3$/G10(FeNaY) | H$_2$O | 6 | 5.7 | 12.5 | 100 | I | K | 49 | — | — |
| G12 | | material above | | | 550 | | K | 29 | — | — |

| Description #: CATALYST & System & Designation & (Salt/Zeolite) | Structure Cond- itions Pore vol cc/g$^{g)}$ | Temp.$^{a)}$ | pH 1% aq.$^{h)}$ | Basicity Resulting INDICATOR COLORS (i) | | | |
|---|---|---|---|---|---|---|---|
| | | | | 4-nitro- aniline/DMSO | 4-chloro aniline/DMSO | 4-nitro- aniline/benzene | 4-chloro- aniline/benzene |
| G1 Ru(NO)(NO$_3$)$_3$/NaY | 100 | | | | | | |
| G2 Ru(NO)(NO$_3$)$_3$/NaY | 550 | 0.31 | 7 | black(o) | nd | nd | black |

TABLE 3-continued

Illustrative Embodiments, Part G.
(Footnotes are those of Part A)

| | | | | | | | | |
|---|---|---|---|---|---|---|---|---|
| G3 | K$_2$CO$_3$/G2(Ru/NaY) | 100 | | | | | | |
| G4 | matl above | 550 | 0.12 | 10 | blackish grn | nd | nd | dp purple |
| G5 | Cu(NO$_3$)$_2$/NaY | 100 | — | 7 | yellow | nd | nd | brown |
| G6 | matl above | 550 | — | 7 | brownish | nd | nd | black |
| G7 | K$_2$CO$_3$/G5 CuNay | 100 | — | 10 | dk green | nd | nd | deep purple |
| G8 | material above | 550 | — | 11 | dark green | nd | nd | deep purple |
| G9 | Fe(NO$_3$)$_3$/NaY | 100 | — | 7 | orng-yellow | nd | nd | amber |
| G10 | matl above Fe/NaY | 550 | — | 8 | Orng-yellow | nd | nd | rose |
| G11 | K$_2$CO$_3$/G10(FeNaY) | 100 | — | 10 | green | nd | nd | rose |
| G12 | matl above | 550 | — | 11 | blue green | nd | nd | rose |

ISOMERIZATION PROCESS

Background

Double bond isomerization is a reaction catalyzed by basic and acidic catalysts. Basic catalysts are normally more selective, since they do not generate cations which can undergo skeletal isomerizations. The instant compositions, particularly the more basic of the instant compositions are particularly useful for double bond isomerization. When compared to a standard sodium exchanged zeolite Y, the instant compositions containing lesser amounts of excess base, say up to about 2 base equivalents per supercage, show less hydrogen transfer, resulting in less alkane make. The more basic of the instant compositions, say those containing greater than 2 base equivalents per supercage, not only show very low alkane make, but also show significantly less cracking than the sodium Y zeolite and very low aromatic make. Decrease in cracking activity is consistent with a decrease in acid function.

The instant compositions are thus particularly useful for the isomerization of additive range (C$_4$ to C$_8$) olefins and detergent range (C$_{10}$ to C$_{18}$) olefins, although higher range olefins can be isomerized. Particularly desired feedstocks to be isomerized are alpha olefins. Isomerization is carried out in a gas or liquid phase at isomerization conditions. Isomerization conditions typically include a temperature in the range of from about 0° C. to about 500° C.; preferably from about 100° C. to about 150° C.; a pressure in the range of from about 1 psig to about 2000 psig and a weight hourly space velocity in the range of from 0.1 to about 20.

Catalyst Preparation

The catalysts utilized were prepared as follows:

I. Comparative NaY Zeolite

Baylith CP-190 NaY zeolite (straight out of the can) was calcined at 500° C. for one hour in flowing nitrogen.

II. Low Base Composition

Baylith CP-190 NaY zeolite was dried in a 100° C. vacuum oven for 16 hrs. 125 Grams of this dried NaY zeolite was impregnated with 4.81 g of potassium carbonate (MCB ACS reagent) dissolved in 62.4 cc of deionized water. The zeolite was mixed in a dish during impregnation and then dried 16 hrs in a 100° C. vacuum oven. This dried material was calcined at 550° C. for 55 minutes in flowing nitrogen. This material contained about 1.8 equivalents of potassium per zeolite supercage.

III. High Base Composition

Baylith CP-190 NaY zeolite was dried in a 100° C. vacuum oven for 16 hrs. 61.7 Grams of this dried NaY zeolite was impregnated with 36.53 g of potassium carbonate (MCB ACS reagent) dissolved in 61 cc of deionized water. The zeolite was mixed in a dish during impregnation and then dried 66 hrs in a 100° C. vacuum oven. The dried zeolite was pressed in bags in an isostatic press at 20,000 psi for 2 minutes. It was then ground and sieved to 16–30 mesh particles. These particles were calcined at 550° C. for one hour in flowing nitrogen. This material contained about 20 equivalents of potassium per zeolite supercage.

Catalyst Testing

Isomerization catalysts were tested in a stainless steel flow reactor measuring 14.75" in length and 0.625" in internal diameter. The reactor was packed bottom to top as follows: a small wad of glass wool, 33 cc of catalyst, a small wad of glass wool, 25 cc 80 grit silicon carbide, followed by another small wad of glass wool. The reactor was operated in a vertical mode in an upright furnace. The feed entered from the top. During isomerization the reactor was operated at 400° C. for one hour with a nitrogen flow rate of 20 l/h and a 1-octene flow rate as indicated in Table 4. After one hour of operation a gas sample was taken and analyzed and the results reported in Table 4. Organic liquid which had been collected in a dry ice trap for the duration of the run was also analyzed and the results reported in Table 4.

TABLE 4

| | Products | | | |
|---|---|---|---|---|
| Catalyst | 1-Octene Feed | 1-Octene | 2-Octene | 3-Octene | Aromatics |
| NaY | 5.7g/h | 67.6 | 15.7 | 12.0 | 0.19 |
| Low Base | 6.1g/h | 89.5 | 3.6 | 3.9 | 0.05 |
| High Base | 5.2g/h | 47.5 | 19.1 | 32.1 | none |

| | Products | | |
|---|---|---|---|
| | Gaseous Cracking < Products | Liquid[a] Cracking Products | n-Octane[b] |
| NaY | 0.55 | 1.03 | 2.82 |
| Low Base | 0.87 | 0.9 | 1.48 |
| High Base | 0.04 | 0.0 | 1.3 |

[a]Defined as new material eluting before n-octane elution.
[b]gc analysis of feed indicated about 1.32% n-octane impurity As can be seen from the Table, the instant compositions show substantially no alkane make when compared to NaY zeolite. The high base composition also shows more isomerization activity than NaY zeolite and shows almost no cracking activity. Further analysis shows skeletal isomerization characteristic of acid catalysis in the sodium exchanged zeolite Y products, and not in the high base products. The lack of skeletal isomerization and cracking in the high base case confirm the virtual absence of acid sites in this basic zeolite. At the high base loadings, the instant composition gave a selectivity of or greater to olefin double bond isomerization, while the standard ion exchanged NaY gave a selectivity of less than 87%.

We claim:

1. A process for preparing a composition-of-matter comprising a zeolite and an alkali metal compound which comprises impregnating a zeolite with an aqueous solution of an alkali metal salt having an oxygen-containing anion other than a hydroxide, wherein the sum of said alkali metal impregnated into the zeolite and any metal cation exchanged into the zeolite is in excess of that required to provide a fully metal cation-exchanged zeolite, drying the thus impregnated zeolite and calcining the zeolite at a temperature ranging from about 150° C. to about 850° C.

2. A process for preparing a composition-of-matter comprising a zeolite and an alkali metal compound which comprises impregnating a zeolite with an aqueous solution of an alkali metal salt other than a hydroxide wherein said alkali metal salt is thermally decomposable upon calcination in the presence of said zeolite to provide an alkali metal-oxygen-containing moiety at a temperature which is less than that at which the zeolite crystallinity is lost and wherein the sum of said alkali metal impregnated into the zeolite and any metal cation exchanged into the zeolite is in excess of that required to provide a fully metal cation-exchanged zeolite, drying the thus impregnated zeolite and calcining the zeolite at a temperature in excess of the temperature at which the alkali metal salt decomposes and at a temperature which is less than that at which the zeolite crystallinity is lost to decompose said alkali metal salt to provide the alkali metal-oxygen-containing moiety.

3. The process of claim 1 or 2 wherein the calcination is carried out at a temperature ranging from about 200° C. to about 750° C.

4. The process of claim 3 wherein the calcination is carried out at a temperature ranging from about 200° C. to about 600° C.

5. The process of claim 1 or 2 wherein the sum of the amount of the alkali metal in said compound and any metal cation exchanged into the zeolite is in excess of about 1.05 times the amount required to provide a fully metal cation-exchanged zeolite.

6. The process of claim 5 wherein the sum of the amount of the alkali metal in said compound and any metal cation exchanged into the zeolite is in excess of about 1.1 times the amount required to provide a fully metal cation-exchanged zeolite.

7. The process of claim 6 wherein the sum of the amount of the alkali metal in said compound and any metal cation exchanged into the zeolite is in excess of about 1.2 times the amount required to provide a fully metal cation-exchanged zeolite.

8. The process of claim 1 or 2 wherein the alkali metal salt is selected from potassium carbonate, potassium bicarbonate, potassium oxalate, potassium acetate and mixtures thereof.

* * * * *